(12) United States Patent
Dieterle et al.

(10) Patent No.: US 12,191,133 B2
(45) Date of Patent: Jan. 7, 2025

(54) MASS SPECTROMETRY METHOD FOR IDENTIFYING AND/OR AUTHENTICATING A SAMPLE

(71) Applicant: ORVINUM AG, Magden (CH)

(72) Inventors: Frank Jochen Dieterle, Binningen (CH); Timm Fabian Manfred Hettich, Freiburg (DE); Christian Berchtold, Rheinfelden (CH); Gotz Schlotterbeck, Efringer-Kirchen (DE); Markus Ehrat, Magden (CH)

(73) Assignee: ORVINUM AG, Magden (CH)

( * ) Notice: Subject to any disclaimer, the term of this patent is extended or adjusted under 35 U.S.C. 154(b) by 558 days.

(21) Appl. No.: 17/610,010

(22) PCT Filed: May 8, 2020

(86) PCT No.: PCT/EP2020/062869
§ 371 (c)(1),
(2) Date: Nov. 9, 2021

(87) PCT Pub. No.: WO2020/229346
PCT Pub. Date: Nov. 19, 2020

(65) Prior Publication Data
US 2022/0199389 A1    Jun. 23, 2022

(30) Foreign Application Priority Data
May 10, 2019    (EP) .................................. 19173824

(51) Int. Cl.
*H01J 49/36*    (2006.01)
*H01J 49/00*    (2006.01)
(Continued)

(52) U.S. Cl.
CPC ........ *H01J 49/165* (2013.01); *H01J 49/0036* (2013.01); *G01N 33/146* (2013.01);
(Continued)

(58) Field of Classification Search
CPC .. H01J 49/165; H01J 49/0036; G01N 33/146; G01N 33/4833; G01N 33/49; G01N 33/493; G01N 33/94; G01N 33/6848
(Continued)

(56) References Cited

U.S. PATENT DOCUMENTS 8,829,429 B2 * 9/2014 Geyer ................ G01N 30/7233
250/281
2009/0065688 A1 3/2009 Hashimoto et al.

FOREIGN PATENT DOCUMENTS

JP    2009-63389    3/2009
JP    2016-206190    12/2016
(Continued)

OTHER PUBLICATIONS

Chambers, et al ("Systematic and comprehensive strategy for reducing matrix effects in LC/MS/MS analyses" J. Chromatography B: Biomed Sci. Appl., 852(1-2), 2007, 22-34). (Year: 2007).*
(Continued)

*Primary Examiner* — Michael Maskell
(74) *Attorney, Agent, or Firm* — Buscher Patent PLLC

(57) ABSTRACT

The present invention relates to a method for identifying and/or authenticating a sample, comprising adding at least one chemical compound to the sample, determining a level of the at least one compound after addition to the sample; comparing the level of the at least one compound to a reference level and identifying the sample based on the comparison with the reference sample and the effect of the sample on the level of the at least one compound. The invention further relates to the use of the at least one compound in the method for identifying and/or authenticating a sample. Further, the invention relates to the use of a kit comprising the at least one compound in the inventive method. In addition, the invention relates to a composition comprising the at least one compound. Further, the invention
(Continued)

Figure 1:
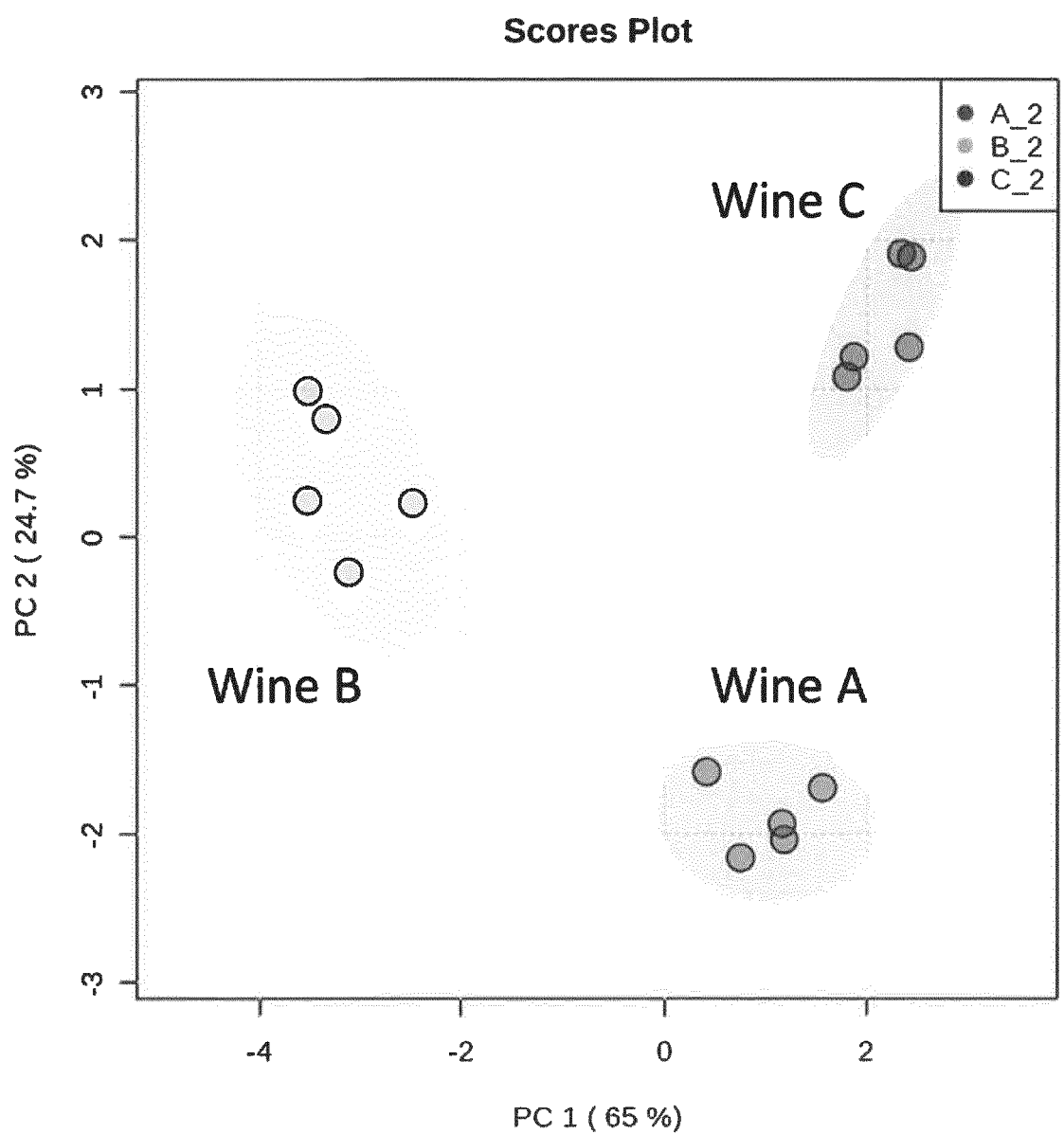

relates to a kit comprising the compositions provided herein, e.g. for calibrating the methods provided herein and/or the instruments employed in the methods provided herein.

27 Claims, 8 Drawing Sheets

(51) Int. Cl.
    *H01J 49/16*     (2006.01)
    *G01N 33/14*     (2006.01)
    *G01N 33/483*     (2006.01)
    *G01N 33/49*     (2006.01)
    *G01N 33/493*     (2006.01)

(52) U.S. Cl.
    CPC ......... *G01N 33/4833* (2013.01); *G01N 33/49* (2013.01); *G01N 33/493* (2013.01)

(58) Field of Classification Search
    USPC ........................................ 250/281, 282, 288
    See application file for complete search history.

(56) References Cited

FOREIGN PATENT DOCUMENTS

| WO | WO 2016/181299 A1 | 11/2016 |
|---|---|---|
| WO | WO 2016/196181 A1 | 12/2016 |

OTHER PUBLICATIONS

E. Chambers et al., "Systematic and comprehensive strategy for reducing matrix effects in LC/MS/MS analyses," *Journal of Chromotography B*, vol. 852, Issues 1-2, Jun. 1, 2007, pp. 22-34.

F. Biasioli et al., "Direct-injection mass spectrometry adds the time dimension to (B)VOC analysis," *Trends in Analytical Chemistry*, vol. 30, No. 7, Jul.-Aug. 2011, pp. 1003-1017.

H. Trufelli et al., "An Overview of Matrix Effects in Liquid Chromatography-Mass Spectrometry," *Mass Spectrometry Reviews*, May-Jun. 2011, vol. 30, No. 3, pp. 491-509.

A. Furey et al., "Ion suppression: A critical review on causes, evaluation, prevention and applications," *Talanta*, vol. 115, Oct. 15, 2013, pp. 104-122.

J. Laaks et al., "Fingerprinting of red wine by headspace solid-phase dynamic extraction of volatile constituents," *Analytical and Bioanalytical Chemistry*, 403, pp. 2429-2436 (2012).

J. Rubert et al., "Metabolic fingerprinting based on high-resolution tandem mass spectrometry: a reliable tool for wine authentication?" *Analytical and Bioanalytical Chemistry*, 406, pp. 6791-6803 (2014).

D. Luykx et al., "An overview of analytical methods for determining the geographical origin of food products," *Food Chemistry*, vol. 107, (2008), pp. 897-911.

\* cited by examiner

MASS SPECTROMETRY METHOD FOR IDENTIFYING AND/OR AUTHENTICATING A SAMPLE

The present invention relates to a method for identifying and/or authenticating a sample, comprising adding at least one chemical compound to the sample, determining a level of the at least one compound after addition to the sample; comparing the level of the at least one compound to a reference level and identifying the sample based on the comparison with the reference sample and the effect of the sample on the level of the at least one compound. The invention further relates to the use of the at least one compound in the method for identifying and/or authenticating a sample. Further, the invention relates to the use of a kit comprising the at least one compound in the inventive method. In addition, the invention relates to a composition comprising the at least one compound. Further, the invention relates to a kit comprising the compositions provided herein, e.g. for calibrating the methods provided herein and/or the instruments employed in the methods provided herein.

BACKGROUND OF THE INVENTION

The identification or authentication of a sample is tedious, expensive and time consuming. This particularly holds true for samples with a complex composition, e.g. foodstuff (for instance wine), pharmaceutical compositions, or body fluids. Such samples may comprise numerous metabolites, small chemicals, lipids, peptides, nucleic acids and/or proteins. The prior art methods are laborious and time consuming:

For example, WO 2016/196181 A1 relates to metabolomics and lipidomics, and to the analysis of metabolite and lipids in simple and complex mixtures. More specifically, WO 2016/196181 relates to a mass spectrometry system using data independent acquisition and having quadrupole and ion mobility separation capabilities for the identification and quantification of metabolites and lipids. WO 2016/196181 discloses that a quadrupole; an ion mobility spectrometer; and a mass spectrometer are coupled together, optionally including an HPLC separation for the sample identification.

In addition, WO 2016/181299 describes a top down method for the investigation of peptides and proteins utilizing an ion source to generate a plurality of precursor peptide or protein ions from a sample solution containing at least one peptide or protein and also suggests using direct infusion into the ion source.

Further, Mann (Nature Reviews Molecular Cell Biology volume 17, page 678 (2016)) discloses strategies for the unbiased detection of all substances present in the sample. This type of analysis is often confined to a few specialized laboratories. Time consuming and cost intensive sample preparation technologies such as depletions, digestions, chromatographic separations and/or high resolution mass spectrometry need to be performed in order to detect the full spectrum of substances. In order to identify e.g. the authentic sample from the potential counterfeit, the generation of quantitatively accurate and highly reproducible datasets is required in which the same proteins or metabolites are quantified across a large number of samples.

One factor that renders the identification of a complex sample difficult is the interference effect caused by components/substances of the sample, e.g. the matrix and ion suppression and enhancement effects:

In mass spectrometry, detection interference effects frequently lead to ion suppression or enhancement phenomena, induced by the presence in the matrix of volatile, but also non volatile compounds able to change the efficiency of analyte droplet formation (or evaporation) as well as the amount of the analyte ions formed in the gas phase that reaches the detector (T. M. Annesley, Clin. Chem. 49 (2003) 1041). The different phenomena potentially induced by the matrix components dramatically affect the method performance in terms of detection capability, selectivity, repeatability, accuracy, linearity of response (signal vs. concentration) and limit of quantification. Furthermore, also due to the spectra modifications brought by ion suppression or enhancement phenomena, it is hard to build a spectrum library. In addition, the lack of fragment ions in full-scan spectra significantly reduces the library information.

Ion suppression and enhancement affects both identification and determination of analytes. It can lead to false negative diagnostics, when it precludes detection of analytes present, but also false positive ones when, for instance, the level of the internal standard (I.S.) undergoes a suppression greater than that of the analyte (F. Gosetti et al./J. Chromatogr. A 1217 (2010) 3929-3937). So for instance in the analysis of clenbuterol in urine, the percentage of ion suppression was shown to range from 37% at the analyte concentration level of 93_gL-1 to 69% for concentration of 45_L-1 (T. M. Annesley, Clin. Chem. 49 (2003) 1041).

Also the choice of positive ion mode (PI) or negative ion mode (NI) modes can affect the signal. When the species can ionize both in PI and NI modes and sensitivity is not an issue, the use of NI mode is suggested because more selective and associated to lower matrix effects. So for instance, when ESI (NI mode) was used in the determination in environment and wastewaters of 37 pesticides (herbicides, insecticides and fungicides), the signal suppression, with only few exceptions, was not significant, in contrast with that observed in PI mode (J. M. Marin, E. Gracia-Lor, J. V. Sancho, F. J. Lopez, F. Hernandez, J. Chromatogr. A 1216 (2009) 1410).

Furey (Talanta. 2013 Oct. 15; 115:104-22. doi: 10.1016/j.talanta.2013.03.048. Epub 2013 Apr. 16.) also discloses that the consequences of matrix effects in mass spectrometry analysis are a major issue of concern to analytical chemists.

One further prior art mass spectrometry method is the direct injection mass spectrometry (DIMS). In DIMS, the diluted sample, e.g. a urine sample, is directly infused into ESI-equipped mass spectrometers without any prior chromatographic separation. DIMS exhibits remarkably high ionization suppression (Dunn & Ellis, 2005; Dettmer, Aronov, & Hammock, 2007; Want et al., 2010; Dunn et al., 2011). A 60% ion suppression of internal standards spiked in rat urine was observed in comparison with standards spiked in saline solution despite the removal of salts from urine using online SPE extraction (Dettmer, Aronov, & Hammock, 2007). Due to such hurdles, its use is limited to rapid high-throughput screening purposes when a large number of samples are investigated for fingerprinting or putative identification (Mikami, Aoki, & Kimura, 2012; Zhang et al., 2012a). (Lit: DOI 10.1002/mas.21455 MASS SPECTROMETRIC BASED APPROACHES IN URINE METABOLOMICS AND BIOMARKER DISCOVERY)

A further strategy to identify a sample is disclosed in Khamis (Mass Spectrom Rev. 2017 March; 36(2):115-134. doi: 10.1002/mas.21455. Epub 2015 Apr. 16. This method involves a complex, multi-step approach. An alternative approach is provided by Causon et al. (2019) Analytica Chimica Acta 1052, pp. 179-189. Fingerprinting of wines using liquid chromatography combined with mass spectrometry is suggested.

Accordingly, the methods for identification and/or authentication of a sample are time-consuming and laborious. Thus, the technical problem underlying the present invention is the provision of means and methods for the rapid and reliable identification and/or authentication of a sample (e.g. foodstuff, in particular wine).

The technical problem is solved by provision of the embodiments characterized in the claims.

Accordingly, the present invention relates to a method for identifying and/or authenticating a sample, wherein the method comprises the steps of:

(i) adding at least one compound to the sample, in particular wherein the at least one compound has a variable ionization;

(ii) obtaining a mass spectrum of the at least one compound and determining a level of the at least one compound after addition to the sample;

(iii) comparing the level of the at least one compound determined in (ii) to a reference level, wherein the reference level is a level of the same compound determined after addition to a reference sample; and (iv) identifying the sample based on the comparison in step (iii) and the effect of the sample on the level of the at least one compound.

The present invention solves the above identified technical problem. As documented herein below and in the appended examples, it was unexpectedly demonstrated that the sample is identified based on the effect of the sample on the level of the at least one compound that is added to the sample. As demonstrated herein below, the inventive method allows an easy, fast and reliable identification of samples, e.g. wine, without requiring to determine any or all components/substances of the sample. The methods may also be used to authenticate the sample. For example, the herein provided method allows the easy, fast and reliable determination whether the sample (e.g. the wine sample) is an original or is a counterfeit. The method further allows to determine whether the sample is diluted compared to the original sample. The underlying principal of the invention is to determine the level of the at least one compound that was added to the sample. Thus, the inventive method comprises adding at least one compound to the sample. In the appended examples, the following exemplary compounds are added to the samples: Sulfaguanidine, Naproxen sodium, Sulfadimethoxine, Ciprofloxacin, Tetracycline hydrochloride, Verapamil hydrochloride, Terfenadine, Leucine Enkephalin acetate salt hydrate and Reserpine. The components/substances of the sample may affect the ionization and thus the level of the at least one compound added to the sample in the mass spectrometer. For example, the components or substances of the sample may have an ion suppression or an ion enhancement effect on the at least one compound. The ionization of the at least one compound can be determined by the level.

The prior art discloses that ion suppression negatively affects the detection capability, precision, and accuracy of mass spectrometry methods. It was the genius idea of the inventors to make use of this alleged negative effects and to identify and/or authenticate the sample based on the effect of the sample on the level of the at least one compound. For example, the substances of the sample can have an ion suppression effect, or an ion enhancement effect on the at least one compound, or alternatively may not substantially alter the ionization of the at least one compound. The methods provided herein make use of these effects on the level of the at least one compound in order to identify and/or authenticate the sample by determining the level of the at least one compound. Thus, the inventive method determines the unique pattern of the levels of the at least one compound after addition to the sample. The sample is identified based on the unique pattern of the level of the at least one compound. Such an exemplary method is documented herein below in the appended examples.

In the prior art, the sample is identified based on the substances comprised in the sample and the levels thereof. In contrast, in the method provided herein, the sample is identified based on the level(s) of the at least one compound after addition to the sample and on the effect of the sample on the level(s) of the at least one compound. Thus, within the present invention, the levels of sample components do not need to be determined and are irrelevant for the identification/authentication of the sample. In other words, the sample to be identified/authenticated corresponds to the matrix used in the mass spectrometry method employed herein to which the at least one compound is added.

Thus, herein below is described an inventive concept based on defined compound sets (the at least one compound) added to the sample and subsequently analyzed by mass spectrometry. The analytical level of the at least one compound is influenced by the substances comprised in the sample (matrix). The impact of the sample on the level of the at least one compound is quantified and allows the identification of the sample in comparison to a reference sample, i.e. a standard (e.g. healthy, calibration or authentic sample etc.).

Prior art approaches seek to reduce matrix/ion suppression and enhancement effects, which are caused by complex sample compositions. Such prior art approaches are based on efforts which have a negative impact on the overall analysis time (including sample preparation and chromatographic run time), complexity of analytical equipment and costs. Typical measures to reduce or eliminate matrix and ion suppression or enhancement effects are the depletion of certain interfering components from the matrix, expansion of chromatographic methods, desalting and buffer/solvent changes or introduction of other ionization sources.

The invention reverses the so far negative effects and makes use of them: level reduction/enhancement of one or more libraries of the at least one compound by the complex sample composition is quantified and correlated with the unique sample identity. In that case the unique pattern of a complex sample on the ion suppression or enhancement of one or more libraries of the at least one compound is used as a fingerprint of the sample itself. As described herein below, the libraries of the at least one compound is also referred herein to as a composition comprising the at least one compound. The method provided herein is characterized by e.g. unprecedented minimal sample preparation and run time. A further advantage is multiplexed dose response curves (each compound vs. sample concentration or sample vs. compound concentration) for precise effect quantification. The herein documented examples demonstrate that wines of different origins can be clearly discriminated by using a library of compounds, e.g. using a direct injection mass spectrometry or alternative mass spectrometry methods, with a run time of less than 5 minutes.

Furthermore, the appended examples show that even samples of water can be identified by the herein provided method; see Example 2. In particular, the examples demonstrate that six different water samples were identified/authenticated by obtaining a mass spectrum of the at least one compound. It is also documented herein below that pure water has a different effect on the level of the at least one compound compared to ion containing water. The different ion containing water samples also showed different effects on the at least one compound. Thus, the herein provided methods can identify/authenticate also water samples. Therefore, the herein provided method can be applied to any sample that can be analyzed by mass spectrometry.

Moreover, the examples document that different spirituous beverages are identified. For example, the herein provided method identifies and/or authenticates Gin and Whisky samples; see Example 3. Example 3 uses further compounds compared to Example 1.

Further, the examples document that the use of already one compound in the herein provided method identifies a sample; see Example 4. Accordingly, one compound can identify and/or authenticate the sample by the herein provided method. The addition of additional compounds further improves the robustness, accuracy and resolution of the identification or authentication; see e.g. Example 3. Thus, the herein provided examples render the herein provided subject-matter plausible.

In addition, the Examples demonstrate that the sample can also be identified if the sample already comprises the at least one compound or one of the at least one compound; see e.g. Example 5 below. In other words, the identification and authentication of the sample is possible if the at least one compound is comprised in the sample. For instance, atrazine or quinine was comprised in the sample to be identified; see Example 5. The further addition of atrazine and/or quinine increased the level of these compounds and a particular effect of the sample on the level of the at least one compound could be determined. Thus, the identification and/or authentication of the sample is/are also possible if the sample already comprises the at least one compound or one of the at least one compound.

The inventive methods and the use of the herein provided kits and compositions provide at least the following advantages over the prior art methods. The method provided herein is faster than the prior art methods since the level(s) of the at least one compounds allows the identification of the sample. Therefore, the analysis time can be reduced from about 30 min to less than about 3 min. There is also no need for e.g. isotope labeled standards or for high-resolution mass spectrometry (MS) analyzers. In addition, the method provided herein does not require laborious sample preparation since the sample comprising the at least one compound can directly be injected into the ionization chamber and the response of the at least one compound can directly be measured. For example, the herein provided method does not need a liquid chromatography step. Therefore, the sample preparation is significantly reduced or eliminated. In addition, the method provided herein allows the use of various buffers and solvents. Thus, the method provided herein has fewer limitations concerning sample buffer and solvent compositions. The herein provided method allows further developments. For example, the at least one compound that is added to the sample, can be easily obtained by screening of compound libraries in order to select the most interacting compounds with the substances of the sample at suitable concentrations. Further, the herein provided method is applicable to all kinds of sample and sample mixtures. Accordingly, the herein provided method, uses, kits and compositions solve the underlying technical problem and provide a rapid, cost-effective and reliable identification and/or authentication of a sample.

The invention relates to the aspects and items herein provided below and above. In the following, the aspects of the invention are described in more detail. These explanations relate to the herein provided methods, uses, compositions and kits.

As used herein, "adding at least one compound to the sample" means that at least one compound is added to the sample. Alternatively, this term may also mean that the sample is added to the at least one compound. If more than one compound is added to the sample, the compounds can be premixed before the addition of the compounds to the sample, e.g. the compounds may be comprised in a composition. In such a case, the composition comprising the at least one compound may be added to the sample. Alternatively, the compounds may be added separately to the sample in the method provided herein.

As used herein, the "at least one compound" used or comprised in the embodiments of the present invention may refer to a chemical or biochemical compound. Preferably, the "at least one compound" may be at least one chemical compound. In certain aspects, the compound may have a variable ionization, (may be susceptible to ion suppression effects) and its ions may be in the mass to charge ratio of the MS detection system in use. In particular, the at least one compound may be a chemical or biochemical compound, in particular a small chemical or biochemical compound. For example, the at least one compound may be a peptide, a protein, an oligonucleotide, a DNA strand or the exemplary compounds as provided herein below. As used herein, the "at least one compound" or the "at least one chemical compound" is herein used interchangeably. In particular aspects, the at least one compound has a variable ionization in a mass spectrometer such that the sample (or the substance(s) comprised in the sample) may have an effect on the level of the at least one compound. The polymer chains such as peptides, proteins, oligonucleotides or DNA can be tuned regarding the susceptibility to ion suppression, e.g. by having more or less charged aminoacids, nucleotides etc. Proteins may be analyzed by a top down (whole protein ionization) or bottom-up (digestion and subsequent peptide analysis) approach. It is furthermore known that proteins as well as peptides are susceptible to ion suppression. In other words, the sample has potentially an effect on the level of the at least one compound. As set out above and documented herein below in the appended examples, the inventive concept of the underlying invention is to identify and/or authenticate the sample based on the effect of the sample on the level at least one compound, wherein the effect of the sample on the at least one compound is determined in the mass spectrometer. In other words, the level of the at least one compound that is determined after the addition to the sample allows the identification and/or authentication of the sample.

The skilled person is aware how to determine whether the sample (or the substance(s) comprised in the sample) has/have an effect on the level of the at least one compound. For example, the level of the at least one compound can be determined without adding the at least one compound to the sample. In other words, the level of the at least one compound is determined in the absence of the sample. In a further step, the sample can be added to the at least one compound. In other words, the level of the at least one compound is determined in the presence of the sample. The comparison of the levels of the at least one compound in the presence of the sample or in the absence of the sample identifies whether the sample has an effect on the at least one compound. Thus, the at least one compound has a variable ionization in a mass spectrometer such that the sample has an effect on the level of the at least one compound.

The variable ionization may be determined in the positive or in the negative mode.

The term "ionization" or "ionization efficiency" can herein be used interchangeably. These terms refer to the production of gas phase ions suitable for resolution and determination in the mass analyzer or mass filter of the mass spectrometer. Therefore, the ionization of a particular compound can be determined by determining the level of the particular compound (in particular the ion(s) of the particular compound) in the mass spectrometer. The term "variable ionization" or "variable ionization efficiency" means that at least one of the at least one compound is susceptible to matrix effects (caused by the substances comprised in the sample). In other words, the term "variable ionization" or "variable ionization efficiency" means that the sample (or the substances comprised in the sample) (1) can have an ion suppression effect on the at least one compound, (2) can have an ion enhancement effect on the at least one compound, or (3) can not substantially alter the ionization of the at least one compound. Thus, the variable ionization of the at least one compound also means that the at least one compound has a variable ionization efficiency in presence and absence of the sample. Accordingly and in particular aspects, the at least one compound has a variable ionization in the presence or absence of the sample. Thus, the variable ionization of the at least one compound means that the sample has an effect on the level of the at least one compound. As indicated above, the effect on the level of the at least one compound can be determined by determining the level of the at least one compound in the presence and absence of the sample and comparing these levels to each other. As indicated, the effect on the level of the sample can also be that the sample does not substantially alter the ionization of the at least one compound. The term "substantially not alter the ionization of the at least one compound" or grammatical variants thereof means that the sample has no measurable ion suppression effect or an ion enhancement effect on the at least one compound. Hence, the sample has no measurable effect on a particular compound. Thus, the level of the at least one compound was not altered by the sample.

The term "ion suppression effect" or "ion suppression" refers to the phenomenon in which the ionization efficiency of the at least one compound is decreased by the presence of a substance comprised in the sample. For example, in the following case there is a greater potential for ion suppression or ion enhancement:

if the target analyte(s)/the substances of the sample are present at only trace amounts in sample with complex matrices, if only minimal sample clean-up is preformed, if acid or alkaline buffers or ion pairing agents are present in the LC effluent, and/or if short non-resolving chromatographic runs are used, and/or if no chromatographic separation is performed.

Ion suppression and enhancement is dependent on the compounds used in the methods of the present invention and occurs in the early stages of the ionization process in the ion source. It can be caused by polar and unretained matrix components (e.g. the substances comprised in the sample) or by over-loading of the LC column. Different mechanisms have been proposed to explain the ion suppression and enhancement phenomenon. These include:

(a) competition between matrix components of the sample and analyte ions that are co-eluting in the sprayed solution for access to the droplet surface for gas-phase emission.

(b) matrix interferences that compete for available charge.

(c) matrix that binds to analyte or causes the analyte to co-precipitate.

(d) analyte ions that may be neutralised through gas phase acid/base reactions.

(e) mobile phase additives, and (f) equipment design.

The term "ion enhancement effect" or "ion enhancement" refers to the phenomenon in which the ionization efficiency of the at least compound is increased by the presence of a substance comprised in the sample. The ion suppression effect and the ion enhancement effect can be determined by the level of the particular compound. In particular aspects of the invention, the at least one compound is susceptible to an ion suppression and/or ion enhancement effect of particular or selected substance(s) comprised in the sample. In other words, the level of the at least compound is preferably altered by the substances comprised in the sample. Suitable compounds of the at least one compound added in the method of the invention, in particular having a variable ionization or ionization efficiency, can be provided, e.g. a library of compounds, for (a) compound(s) providing the particular level(s) in the presence of the sample that are suitable for the identification and/or authentication of the sample.

In particular aspects, the at least one compound refers to 1 to 100 compounds, preferably to 1 to 80 compounds, more preferably to 1 to 60 compound, even more preferably to 1 to 50, even more preferably to 1 to 40, even more preferably to 1 to 30, even more preferably to 1 to 20, even more preferably 1 to 15, even more preferably 1 to 12, or even more preferably at least 9 compounds. The term "at least" means that more than the particular number of compounds are added or that the particular number of compounds is added to the sample.

In preferred aspects, the at least one compound refers to more than one compound. In particular aspects, the at least one compound have particular ion suppression or ion enhancement against particular substances/classes of substances of the sample. The at least one compound added to the sample may be distinguishable in the mass spectrum. The at least one compound may have different chemical or physical properties (e.g. log P, pKa, and molecular weight) and allows to get orthogonal information from the sample, comparable to the information obtained from different separation mechanisms in conventional chromatography based methods. In particular aspects, the compounds added in the herein provided method may have a high (e.g. peptides or proteins) or low (e.g. small molecules) molecular weight determined in the mass spectrometer, a different partition coefficient (log P), and/or a different pka. The term is "high" and "low" as used in these aspects mean that different masses may be determined in the mass spectrometer, i.e. the levels of the more than one compound can be resolved in the mass spectrometer. The at least one compound may have a concentration in the sample of at least 5 times the limit of quantification after addition to the sample. In particular, the at least one compound has a concentration in the sample after addition to the sample to suppress and/or enhance the level of the least one compound to about 20% to about 80% in comparison to the level of the same compound determined in the absence of the sample.

In particular aspects, the at least one compound is not comprised in the sample before the addition to the sample. As used herein, the term "is not comprised in the sample" means that a level of the at least one compound could not be determined in the mass spectrometer, which is used for employing the method, before addition of the at least one compound to the sample. Accordingly, the level of the at least one compound is under the limit of detection in such aspects. Preferably, the at least one compound does not occur in the sample.

As shown herein below, the sample can be identified and/or authenticated if the at least one compound is already comprised in the sample before adding the at least one compound to the sample. In such aspects, the at least one compound is added to the sample in such a concentration that the level is increased and the sample has an effect on the level that could be determined in the mass spectrometry. Alternatively, the at least one compound may be added to e.g. two or more aliquots of the sample in two different concentrations and the difference in the levels obtained from the sample is compared to the difference of the level of the signal of a calibration series.

The at least one compound added in the methods of the invention and provided herein (or the herein provided and used kits) may preferably be selected from the group consisting of sulfaguanidine, naproxen sodium, sulfadimethoxine, ciprofloxacin, tetracycline hydrochloride, verapamil hydrochloride, terfenadine, leucine enkephalin acetate salt hydrate and reserpine.

The at least one compound added in the methods of the invention and provided herein (or the herein provided and used kits) may be selected from the group preferably consisting of Leu-enkephalin acetate salt hydrate, Terfenadine, Verapamil hydrochloride, Tetracycline hydrochloride, Diltiazem hydrochloride, Linomycin hydrochloride, Buspirone hydrochloride, Sarafloxacin hydrochloride hydrate, Haloperidol, Trazodone hydrochloride, Ciprofloxacin, Quinine, Ranitidin hydrochloride, Triclocarban, Sulfadimethoxine, Trimethoprim, Amitriptyline hydrochloride, Atenolol, Propranolol hydrochloride, Sulfathiazole, Sulfamethoxazole, Cimetidin, Salbutamol, Melatonin, Naproxen sodium, Atrazine, Sulfaguanidine, Metformin hydrochloride and Reserpine. The herein provided exemplary compounds may also be used as any other salts thereof.

In particular aspects, the at least one compound is sulfaguanidine, naproxen sodium, sulfadimethoxine, ciprofloxacin, tetracycline hydrochloride, verapamil hydrochloride, terfenadine, leucine enkephalin acetate salt hydrate and reserpine. Such compounds are exemplary compounds used in the appended examples. The CAS-numbers are disclosed herein below. Any other compound may be used in the herein provided aspects as long as the compound provides a variable ionization efficiency that could be determined by the level of the compound in the mass spectrometer. Therefore, in particular aspects, the at least one compound is tailored for a particular sample such that the levels of the at least one compound allow the identification and/or authentication of the sample. Suitable compounds may be identified by screening compound libraries by mass spectrometry. The screening methods may select compounds that show an altered ionization caused by the sample. In other words, the at least one compound may preferably be at least one compound that has a variable ionization in a mass spectrometer such that the sample has an effect on the level of the at least one compound as indicated above. For example, the screening method may preferably select compounds, wherein the sample has a matrix effect on the compound, wherein the compounds are commercially available, stable, pure, soluble in the sample, and/or not comprised in the sample.

Further, in the herein provided methods, a quencher may be additionally added to the sample, in particular wherein the quencher is added to the sample at one or more concentrations suitable to calibrate the method and to provide a quality control. Such quencher may also be comprised in the composition or the kit provided herein comprising the at least one compound. The quencher may refer to a standard. Alternatively, the quencher may also increase the quenching effect.

In a further embodiment of the invention, a sample is provided which can be used as a standard for calibration of the methods provided herein. Such a calibration sample may for example comprise known compounds, in particular compounds with known variable ionization and/or known ionization effects such as a known ion suppression effect on the at least one compound, a known ion enhancement effect on the at least one compound or known to not substantially alter the level of the at least one compound. Accordingly, such a sample may be used to calibrate the methods provided herein and the instruments employed in the methods provided herein.

As used herein, a "mass spectrum" refers to a plot of the relative abundances of ions forming a beam or other collections as a function of their m/z values. In the herein provided methods, a "mass spectrum" is obtained of, at least, the at least one compound. The determination of the level and the obtaining of the mass spectrum may be obtained in the positive mode or in the negative mode. In the herein provided methods, a mass spectrum or mass spectra of the at least one compound can be obtained and optionally further mass spectra may also be obtained for the substances of the sample. Since more than one compound may be added to the sample in particular aspects of the invention, a mass spectrum of each of the at least one compound may be obtained. In particular aspects, only the level(s) of the at least one compound is/are determined in the method of the invention. In particular as aspects, the levels of substances comprised in the sample are not determined. Thus, in particular aspects, only the level(s) of the at least one compound is/are determined, wherein the level(s) of the substances that are comprised before the addition of the at least one compound is/are not determined. As described herein below and above, the sample is identified and/or authenticated based on the effect of the sample on the level of the at least one compound. Thus, the level of the at least one compound may be sufficient for the identification and/or authentication of the sample. In some aspects of the invention, the level(s) of the substances comprised in the sample may also be determined. Such levels may provide an internal standard, e.g. to the mass spectrum.

In particular aspects, the mass spectrum is obtained by a mass spectrometry method using ionization sources and interfaces. Preferably, the mass spectrum is obtained by direct injection mass spectrometry. In particular, the mass spectrum is obtained by a mass spectrometer coupled to an ion source, in particular an electrospray ionization.

The mass spectrum may be obtained by various MS techniques as indicated above. Sample preparation methods comprise techniques for lysis, fractionation, digestion of the sample into peptides, depletion, enrichment, dialysis, desalting, alkylation and/or peptide reduction. However, these steps are optional since one advantage of the herein provided method is that such a method does not require pretreating as also indicated below. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The sample may be directly injected into the ion source of the mass spectrometer in particular aspects of the invention. The herein appended examples show a method, wherein no separation step was used. In such aspects, the sample used in step (i) does not experience a separation step. This means that, for example, the sample was not enriched for particular substance(s) before the addition and the determination of the levels of the at least one compound. For example, the level(s) in step (ii) of the herein provided methods are determined without a chromatographic separation, e.g. liquid chromatography.

The mass spectrum may also be obtained by Matrix Assisted Laser Desorption Ionization (MALDI) in certain embodiments. As long as the levels of the sample, the reference sample and the at least one compound are determined by the same ionization and mass spectrometry method, e.g. MALDI-MS, the sample can be identified and/or authenticated by the herein provided method since the impact of the ionization technique and/or mass spectrometry method is similar on the level of the sample and the reference level. Thus, the effect of the sample on the level of the at least one compound can also be determined in MALDI-MS. Matrix Assisted Laser Desorption Ionization (MALDI) may be used in the methods provided herein.

Further, as described in Journal of Chromatography A, 1493 (2017) 57-63 and in Food Chemistry 244 (2018) 128-135, an on-line sample preparation, to remove e.g. certain substance classes such as salts which could have an impact on the MS system, as well as a post column addition of certain agents to improve the detection and signal of compounds of interest are known. It is therefore conceivable herein that an initial sample preparation e.g. in form of a chromatographic step is performed to remove potentially disturbing substance classes and add, similar to a post column derivatization method, the at least one compound. Thus, the mass spectrum may also be obtained by applying a chromatographic separation and subsequently adding the at least one compound.

As used herein, the "sample" refers to a sample comprising substances to which the at least one compound is added in order to identify and/or authenticate the sample. The sample used herein may have a complex composition comprising substances, e.g. numerous metabolites, chemicals, lipids, peptides, nucleic acids and/or proteins. The term "sample" may refer to the matrix. Since the provided methods are mass spectrometry methods, the sample is a sample that is suitable to be analyzed by a mass spectrometer. Thus, the herein provided method is a mass spectrometry method for identifying and/or authenticating a sample. The sample may be a liquid sample. However, the sample may also be a solid sample that is suitable to be analyzed by mass spectrometry or that was made suitable to be analyzed by mass spectrometry. The skilled person is aware how to prepare a sample such that it is suitable to be analyzed in a mass spectrometer. For example, the substances comprised in a (solid) sample can be extracted or be dissolved in order to prepare a (liquid) sample that can be analyzed in a mass spectrometer. For example, as described in Journal of Chromatography A 1617 (2020) 460830, solid samples can be analyzed by LC-MS after a sample preparation method as know by the person skilled in the art. For instance, the solid sample can be pulverized e.g. after freezing with liquid nitrogen to avoid the heat loss of substance of interest, in a cutting mill, followed by an extraction step such as e.g. a solvent extraction or any other extraction/sample preparation method suitable for the substances of interest in the solid sample. To the extract, the at least one or more compound can be added and the sample can be processed by the herein described methods. Therefore, the sample of the herein provided method is not particularly limited as long as the sample can be analyzed by mass spectrometry, or as long as the mass spectrum of the at least one compound that was added to the sample can obtained.

As shown herein below, the herein provided method can also identify water samples. The water sample comprise (a) substance(s) that has/have an effect on the level of the at least on compound. A potential result is also if the sample does not comprise a substance that has an effect on the level of the at least one compound. The same would also hold true for a fraction of a sample. Thus, any sample is suitable to be used in the herein provided method as long as the sample (or the substance(s) comprised in the sample) has/have an effect on the level of the at least one compound as indicated above. The skilled person is aware how to determine whether the sample has an effect on the level of the at least one compound as indicated above. For example, the level of the at least one compound can be determined without adding the at least one compound to the sample. In a further step, the sample can be added to the at least one compound. Thus, the levels of the at least one compound can be determined in the presence and absence of the sample and these levels can be compared to each other. The comparison of the levels identifies whether the sample has an effect of the at least one compound. Thus, any sample could be used in the herein provided methods that has an effect on the level(s) of the at least one compound. In other words, any sample can be used in the herein provided method that provides a matrix effect on the at least one compound.

In particular, the sample is selected from the group consisting of wine, spirituous beverage, foodstuff, processed foodstuff, tea, coffee, herb extract, natural product, natural products extracts, beer, fruit juice (for example orange and apple), a pharmaceutical composition, a formulation of a pharmaceutical, a body fluid, blood, blood plasma, blood serum, and urine. In particular, the sample is a foodstuff. In preferred aspects, the sample is a wine. In more preferred aspects, the sample is a wine, that is the herein referred matrix that has an effect on the at least one compound added to the wine sample. The sample may comprise a single wine or may be a mixture of wines. For example, the sample may be a pooled sample suitable for the use in quality control.

As used herein, the term "reference sample" refers to a known sample, e.g. an authenticated sample, for instance a standard sample. In particular aspects, the sample and the reference sample are from the same sort. For example, if the sample is a wine sample, the reference sample is also a wine sample, in particular a wine sample of know origin, vintage etc. In preferred aspects, the reference sample is an authentic sample. In most preferred aspects and as shown in the appended examples, the reference sample is a wine sample of particular vintage, of a particular grape variety, or from a particular region. As set out herein, the sample may also be a pharmaceutical composition or a formulation of a pharmaceutical. In such a case, the herein provided method may be used to identify whether the pharmaceutical composition or the formulation of a pharmaceutical to be identified is an original or whether the sample is a counterfeit or a diluted sample. The sample may also be a body fluid, blood, blood plasma, blood serum, and urine. In such a case, the herein provided method may be used in the diagnosis, prognosis, risk assessment, risk stratification, monitoring, therapy guidance and/or therapy control of subjects. For example, a substance may be comprised in the sample if a particular condition occurs, e.g. if the subject suffers from a particular condition (for instance a disease or disorder). Such a substance may affect the ionization of the at least one compound after addition to the sample. Thus, such a substance may affect the ionization of the at least one compound after addition to the sample, if the substance is comprised or if the substance is not comprised in the sample. Therefore, the inventive method may be used in the diagnosis, prognosis, risk assessment, risk stratification, monitoring, therapy guidance and/or therapy control of subjects. In particular aspects, the reference sample or the reference level is determined by the same mass spectrometry technique as the level of the at least one compound. Thus, the same mass spectrometry technique, e.g. ESI or MALDI and/or direct injection into the ion source of the mass spectrometer, is used for the reference level/sample and the level of the at least one compound.

In the herein provided methods, a level of the at least one compound after addition to the sample is determined. As used herein, the term "a level of the at least one compound after addition to the sample is determined" or grammatical variants thereof may mean that a level of (an) ion(s) of the at least one compound or (a) fragment(s) thereof are determined. As used herein, it is understood that the level of the at least one compound that is determined or compared herein may refer to a level of (an) ion(s) of the at least one compound or (a) fragment(s) thereof. The same applies for the reference level.

Thus, the method may refer to a method comprising the steps of:
  (i) adding at least one compound to the sample, in particular wherein the at least one compound has a variable ionization;
  (ii) obtaining a mass spectrum of the at least one compound and determining a level of (an) ion(s) of the at least one compound or (a) fragment(s) thereof after addition to the sample;
  (iii) comparing the level of the ion(s) of the at least one compound or the fragment(s) thereof determined in (ii) to a reference level, wherein the reference level is a level (an) ion(s) of the same compound or the fragment (s) thereof determined after addition to a reference sample; and
  (iv) identifying the sample based on the comparison in step (iii) and the effect of the sample on the level of the ion(s) of the at least one compound or the fragment(s) thereof.

As used herein, the term "level" refers to (a) the peak intensity or the integral of the peak determined by the mass spectrometer. In particular, the term "level" refers to the relative abundance(s) of the ions produced in the mass spectrometer. As used herein, the term "a level" refers to one or more levels of the at least one compound. The skilled person is aware that the level determined by mass spectrometry of a particular compound may comprise the levels of (an) ion(s) of the particular compound or (a) fragment(s) thereof. Accordingly, the level of the (at least one) compound may refer to the abundance(s) of the ions produced from the (at least one) compound in the mass spectrometer. Therefore, one level may be obtained for a particular compound or more than one level may be obtained for the particular compound in the aspects of the invention. In particular aspects, more than one compound is added to the sample. In such aspects, the levels of the compounds after addition to the sample are determined in step (ii), and wherein in step (iii) the levels of the compounds are compared to corresponding reference level(s). In particular, the levels of each of the compounds after addition to the sample are determined in step (ii), and wherein in step (iii) the levels of each of the compounds are compared to each corresponding reference level(s).

In certain alternative aspects, the term "level" may also refer to the mass spectrum or mass spectra. In such aspects, the invention may relate to a method comprising the steps of:
  (i) adding at least one compound to the sample, in particular wherein the at least one compound has a variable ionization;
  (ii) determining a mass spectrum of the at least one compound after addition to the sample;
  (iii) comparing the mass spectrum of the at least one compound determined in (ii) to a reference mass spectrum, wherein the reference mass spectrum is a mass spectrum of the same compound determined after addition to a reference sample; and
  (iv) identifying the sample based on the comparison in step (iii) and the effect of the sample on the mass spectrum of the at least one compound.

In the herein provided methods, the level of the at least one compound determined in step (ii) is compared to a reference level. The skilled person understands that this term may mean that the level of the ion(s) of the at least one compound determined in step (ii) is compared to a reference level. In particular aspects, the levels of a particular compound are compared to the reference level or to corresponding reference levels. Thus, the levels of the at least one compound may be compared to the reference levels or to the corresponding reference levels. As used herein, the term "reference level" is a level of the same compound determined after addition to a reference sample. Thus, the term "reference level" means a level which is known and is indicative for a particular sample. The reference level may be determined in the method of the invention or may be known. Thus, the reference level could be comprised in a kit and the levels determined of the sample could be compared to such a reference level.

Purely by way of example of the inventive method and without any limiting character, compounds X and Y are added to sample A in step (i) of the inventive method. A mass spectrum for each compound X and Y is obtained and levels of the compounds X and Y (e.g. several levels for each X and Y) after addition to the sample are determined in step (ii) of the inventive method. In step (iii) of the inventive method, the level(s) of compound X determined in step (ii) is/are compared to (a) reference level(s) of compound X determined after addition to a reference sample. In addition, the level(s) of compound Y determined in step (ii) is/are compared to (a) reference level(s) of compound Y determined after addition to the reference sample. Thus, corresponding levels are compared. Accordingly, the "reference level being a level of the same compound" means that the determined level(s) of the at least one compound is/are compared to (a) corresponding reference level(s), e.g. level(s) of compound X is/are compared to (a) reference level(s) of compound X.

In step (iv) of the inventive method, the sample is identified based on the comparison in step (iii) and on the effect of the sample on the level of the at least one compound. As described herein above and below, the sample (or the substances comprised in the sample) may have a matrix effect on the at least one compound such that sample (1) can substantially not alter the ionization of the at least one compound, (2) can have an ion suppression effect on the at least one compound, or (3) can have an ion enhancement effect on the at least one compound. Such effects either effect the level of the at least one compound such that the level of the at least one compound is increased or decreased, or do substantially not alter the level of the at least one compound. By comparing the level of the least one compound to the reference level, the sample is identified. For example and in particular aspects, a similar or an identical level of the at least one compound compared to the reference level indicates that the sample corresponds to the reference sample; or wherein a difference in the level of the at least one compound as compared to the reference level indicates that the sample does not correspond to the reference sample. As used herein, "different" means that the level of the at least one compound can be increased or decreased compared to the reference level. For example, an increase could be caused by an ion enhancement effect or a decrease could be caused by an ion suppression effect. As indicated, if more than one level is determined for a particular compound of the at least one compound, the levels of the particular compound may be compared to corresponding reference levels. Thus, the inventive method may also relate to a method, wherein similar or identical level(s) of the at least one compound compared to the reference levels indicate that the sample corresponds to the reference sample; or wherein (a) difference(s) in the levels of the at least one compound as compared to the reference level indicates that the sample does not correspond to the reference sample. As also indicated above, more than one level could be determined per compound and more than one compound may be used in the herein provided methods. In such aspects, similar or identical levels of the compounds compared to the reference levels indicate that the sample corresponds to the reference sample; or wherein (a) difference(s) in the levels of the compounds as compared to the reference levels indicate(s) that the sample does not correspond to the reference sample. The skilled person is aware which levels are suitable to be compared to each other and which levels are used to identify the sample since the corresponding reference levels of the reference sample are known. Thus, the most suitable levels (e.g. most abundant levels) could be determined, be compared to the corresponding reference levels and based thereon the sample could be identified. In other words, the levels of the compounds may be weighted in the identification of the sample.

As indicated above and as demonstrated herein below, the ionization efficiency of the at least one compound determines how much ions are produced and could be determined in the mass spectrometer. The sample (or the substances comprised in the sample) determine(s) the ionization efficiency of the at least one compound. Thus, the inventive methods may also relate to a method, wherein the ion suppression efficiency or the ion enhancement efficiency of the at least one compound is determined, and said ion suppression efficiency or said ion enhancement efficiency is compared to the ion suppression efficiency or to the ion enhancement efficiency of the reference sample, and based thereon the sample is identified.

In particular aspects, the inventive method may also relate to a method, wherein in step (iv) the sample is identified based on the particular pattern of ion suppression or ion enhancement of the at least one compound.

In particular aspects of the inventive method, one or more dose response curves are determined. Dilution of the sample and/or of the at least one compound allow to generate multiplexed dose response curves. As used herein, a dose response curve refers to a function of determined levels. The dose response curve may be based on the levels determined in the inventive method. In particular aspects, the dose response curve is based on the levels of different concentrations of the at least one compound; or the dose response curve is based on the levels of the at least one compound after addition to said different concentrations of said sample. For such aspects, in step (i) of the inventive method, different concentrations of the at least one compound are added to the sample, and wherein in step (ii) the levels of the different concentrations of the at least one compound after addition to the sample are determined. Alternatively, in step (i) of the inventive method, the at least one compound is added to different concentrations of the sample (e.g. different dilutions of the sample) and wherein in step (ii) the levels of the at least one compound after addition to the samples are determined. Such levels may be used to generate the dose response as indicated above. As set out above, the at least one compound may be added to the sample in different concentrations. Suitably, the at least one compound has a concentration in the sample of at least 5 times the limit of quantification after addition to the sample. Thus, starting from such a concentration the at least one compound can be added in higher concentrations. In particular aspects, the at least one compound has a concentration in the sample after addition to the sample to suppress and/or enhance the level of the least one compound to about 20% to about 80% in comparison to the level of the same compound determined in the absence of the sample.

The dose response curve can also be based on the levels of the at least one compound after addition to the samples having a different concentration, and said dose response curve is compared to a dose response curve of the reference sample, wherein said dose response curve of the reference sample is based on the reference levels of the at least one compound after addition to the reference samples having a different concentration.

In the herein provided methods, the at least one compound may be adjusted for optimum ion suppression and enhancement effects on the sample. Preferably, the concentration of the at least one compound is selected in a way that the level of the at least one compound is at least 5 times the limit of quantification and the sample causes an effect of up to about 20% signal enhancement or of up to about 80% signal reduction.

In particular aspects, the identification of the sample is the identification of a dilution of the sample as indicated above. Such a method is particularly suitable to identify whether the sample is identical to the original reference sample or whether the sample is diluted compared to the reference sample. Dilution of samples may be important if the sample is, for example, an expensive wine, or if the sample is a pharmaceutical composition, wherein the concentration of the sample may determine the medical efficacy. In such aspects, the dilution of the sample may be identified based on the comparison of the dose response curve of the sample to the dose response curve of the reference sample. In particular aspects, the dose response curves may be based on the levels of the different concentrations of the at least one compound determined in the sample and determined in the reference sample. Alternatively, the dose response curves may be based on the levels of the least one compound determined in the different concentrations of the sample and determined in the different concentrations of the reference sample.

The invention further relates to a method for identifying a dilution of the sample by comparing the dose response curves of the reference sample and the sample vs. constant or varying concentrations of the at least one compound.

As shown in the appended examples, the herein provided method may preferably be performed in the order of the steps (i), (ii), (iii) and (iv) as recited herein above.

The invention further relates to the use of the method and the use of the at least one compound in the herein provided methods. The invention further relates to a kit and the use of a kit in the herein provided methods. All the explanations, definitions and information provided herein above and below also apply these aspects of the invention. In the following, further particular embodiments of these aspects are described.

The invention relates to the use of the at least one compound described herein. In particular, the invention relates to the use of the at least one compound having a variable ionization efficiency. The invention further relates to a composition comprising 1 to 100 compounds, preferably to 1 to 80 compounds, more preferably to 1 to 60 compound, even more preferably to 1 to 50, even more preferably to 1 to 40, even more preferably to 1 to 30, even more preferably to 1 to 20, even more preferably 1 to 15, even more preferably 1 to 12, or even more preferably at least 9 compounds, or 29 compounds. The inventive composition may comprise compounds of different classes of compounds. In the appended examples, a composition was used comprising 9 compounds. Further, in the appended examples, a composition was used 29 compounds or one compound. Thus, such compositions are preferred. It is preferred that composition comprising the at least one compound and its use thereof in the herein provided method. In particular, the herein provided composition comprises sulfaguanidine, naproxen sodium, sulfadimethoxine, ciprofloxacin, tetracycline hydrochloride, verapamil hydrochloride, terfenadine, leucine enkephalin acetate salt hydrate and reserpine. Further, the composition may comprise Leu-enkephalin acetate salt hydrate, Terfenadine, Verapamil hydrochloride, Tetracycline hydrochloride, Diltiazem hydrochloride, Linomycin hydrochloride, Buspirone hydrochloride, Sarafloxacin hydrochloride hydrate, Haloperidol, Trazodone hydrochloride, Ciprofloxacin, Quinine, Ranitidin hydrochloride, Triclocarban, Sulfadimethoxine, Trimethoprim, Amitriptyline hydrochloride, Atenolol, Propranolol hydrochloride, Sulfathiazole, Sulfamethoxazole, Cimetidin, Salbutamol, Melatonin, Naproxen sodium, Atrazine, Sulfaguanidine, Metformin hydrochloride and Reserpine or any other salt thereof.

This composition may preferably be comprised in the kit of the invention. The at least one compound may be comprised in the composition or may also be added separately to the sample.

The invention further relates to a kit and the use of the kit in the herein provided methods. The kit comprises the herein described at least one compound, and optionally (a) reference level(s) of the reference sample in the method of any one of the preceding items. Thus, the reference level may be comprised in the kit, e.g. in the form of instructions. In a further aspect, a kit is provided comprising the standard sample provided herein, in particular for calibrating the instruments employed in the methods provided herein. Accordingly, such a kit may comprise a standard sample as described herein comprising known compounds and, in addition, instructions to calibrate instruments which are suitable to be employed in the provided methods.

As used herein, the terms "comprising" and "including" or grammatical variants thereof are to be taken as specifying at least the stated features, integers, steps or components but do not preclude the addition of one or more additional features, integers, steps, components or groups thereof. This term encompasses the terms "consisting of" and "consisting essentially of" that are understood to specify only the stated feature, integers, steps or components to the exclusion of any additional features.

Thus, the terms "comprising"/"including"/"having" mean that any further component (or likewise features, integers, steps and the like) can/may be present.

The term "consisting of" means that no further component (or likewise features, integers, steps and the like) is present.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The term "about" preferably refers to ±10% of the indicated numerical value, more preferably to ±5% of the indicated numerical value, and in particular to the exact numerical value indicated.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 amino acids" refers to the range of 23 to 28 amino acids, in particular the range of 24 to 26 amino acids, and preferably refers to the specific value of 25 amino acids.

In particular aspects, the present invention relates to:
1. A method for identifying and/or authenticating a sample, wherein the method comprises the steps of:
   (i) adding at least one compound to the sample, in particular wherein the at least one compound has a variable ionization;
   (ii) obtaining a mass spectrum of the at least one compound and determining a level of the at least one compound after addition to the sample;
   (iii) comparing the level of the at least one compound determined in (ii) to a reference level, wherein the reference level is a level of the same compound determined after addition to a reference sample; and
   (iv) identifying the sample based on the comparison in step (iii) and the effect of the sample on the level of the at least one compound.
2. The method of item 1, wherein the level is (a) mass spectrometry signal level(s), in particular wherein the level is the abundance determined in the mass spectrum.
3. The method of any one of the preceding items, wherein the sample has an ion suppression, or has an ion enhancement effect on the at least one compound or wherein the sample does not substantially alter the ionization of the at least one compound.
4. The method of any one of the preceding items, wherein the ion suppression efficiency or the ion enhancement efficiency of the sample on the at least one compound is determined, and said ion suppression efficiency or said ion enhancement efficiency is compared to the ion suppression efficiency or to the ion enhancement efficiency of the reference sample on the same at least one compound, and based thereon the sample is identified.

5. The method of any one of the preceding items, wherein a similar or an identical level of the at least one compound compared to the reference level indicates that the sample corresponds to the reference sample; or wherein a difference in the level of the at least one compound as compared to the reference level indicates that the sample does not correspond to the reference sample.

6. The method of any one of the preceding items, wherein in step (i) 1 to 15 compounds are added.

7. The method of any one of the preceding items, wherein the compounds are susceptible to an ion suppression and/or ion enhancement effect of particular substances comprised in the sample.

8. The method of any one of the preceding items, wherein in step (ii) the level of each of the at least one compound is determined, and wherein in step (iii) the level of each of the at least one compound is compared to each reference level.

9. The method of any one of the preceding items, wherein the sample is a pooled sample suitable for the use in quality control.

10. The method of any one of the preceding items, wherein the sample is selected from the group consisting of wine, spirituous beverage, foodstuff, processed foodstuff, tea, coffee, herb extract, natural product, natural products extracts, beer, fruit juice (for example orange and apple), a pharmaceutical composition, a formulation of a pharmaceutical, a body fluid, tissue extract, blood, blood plasma, blood serum, and urine, in particular wherein the sample is wine.

11. The method of any one of the preceding items, wherein the reference sample allows the identification and/or authentication of the sample.

12. The method of any one of the preceding items, wherein the reference sample is an authentic sample or a sample with a known composition.

13. The method of any one of the preceding items, wherein the reference sample is a wine sample of particular vintage, of a particular grape variety, or from a particular region, or from a particular producer.

14. Use of at least one compound having a variable ionization in the method of any one of the preceding items.

15. Use of a kit comprising at least one compound having variable ionization, and optionally (a) reference level(s) of the reference sample in the method of any one of the preceding items.

16. The method of any one of items 1 to 13, wherein the sample comprises known compounds with known variable ionization and/or known ionization effects such as a known ion suppression effect on the at least one compound, a known ion enhancement effect on the at least one compound or known to not substantially alter the level of the at least one compound, wherein the sample is used to calibrate the method and/or the instruments employed in any one of claims 1 to 13.

The present invention is further described by reference to the following non-limiting figures and examples.

Figure 2:
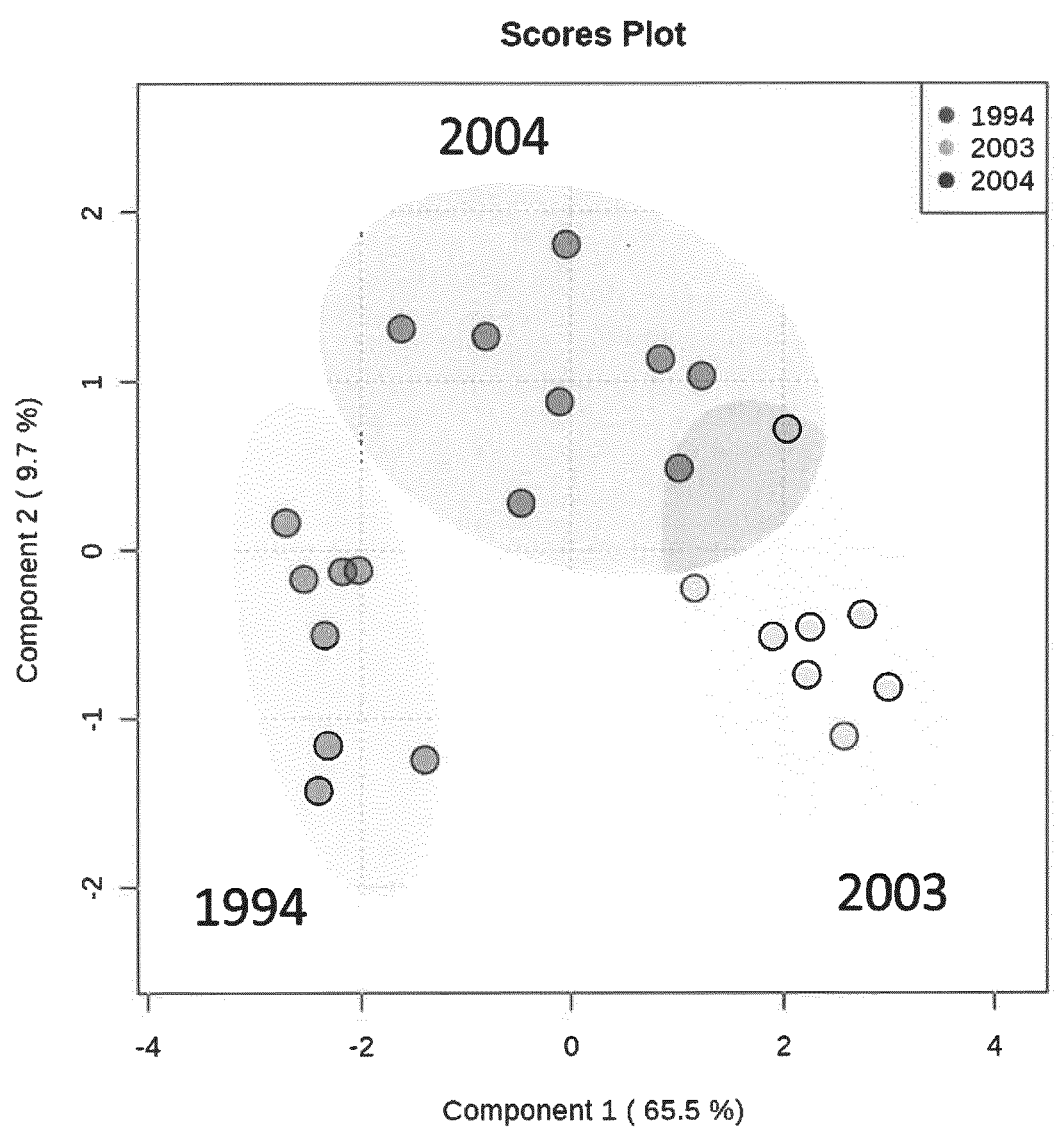

FIGS. 1 and 2: Scores Plots for the first two exemplary compounds from Example 1.

Figure 3:
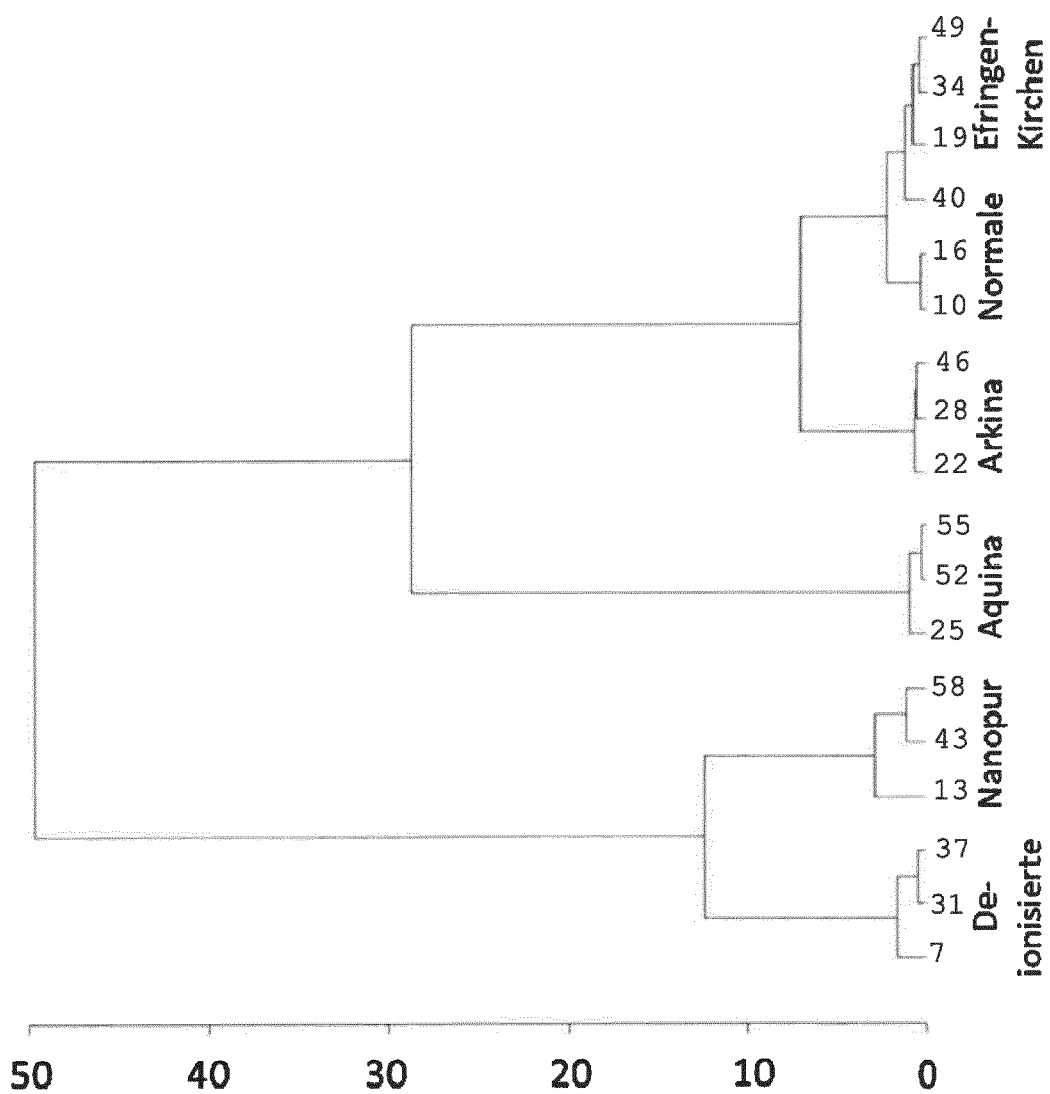

FIG. 3: Results of Hierarchical Cluster Analysis (similarity is represented by the x-axis).

Figure 4:
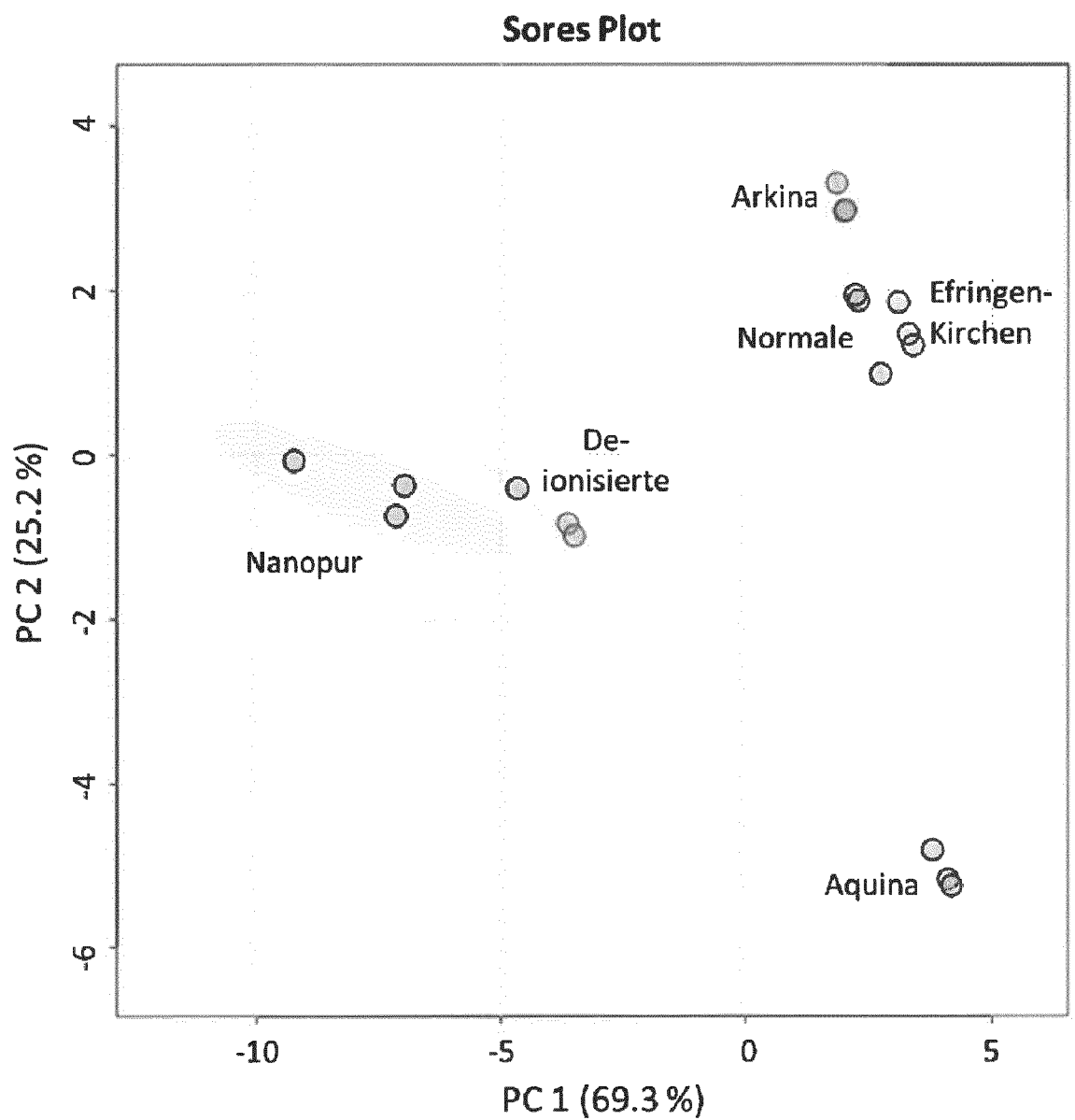
Figure 5:
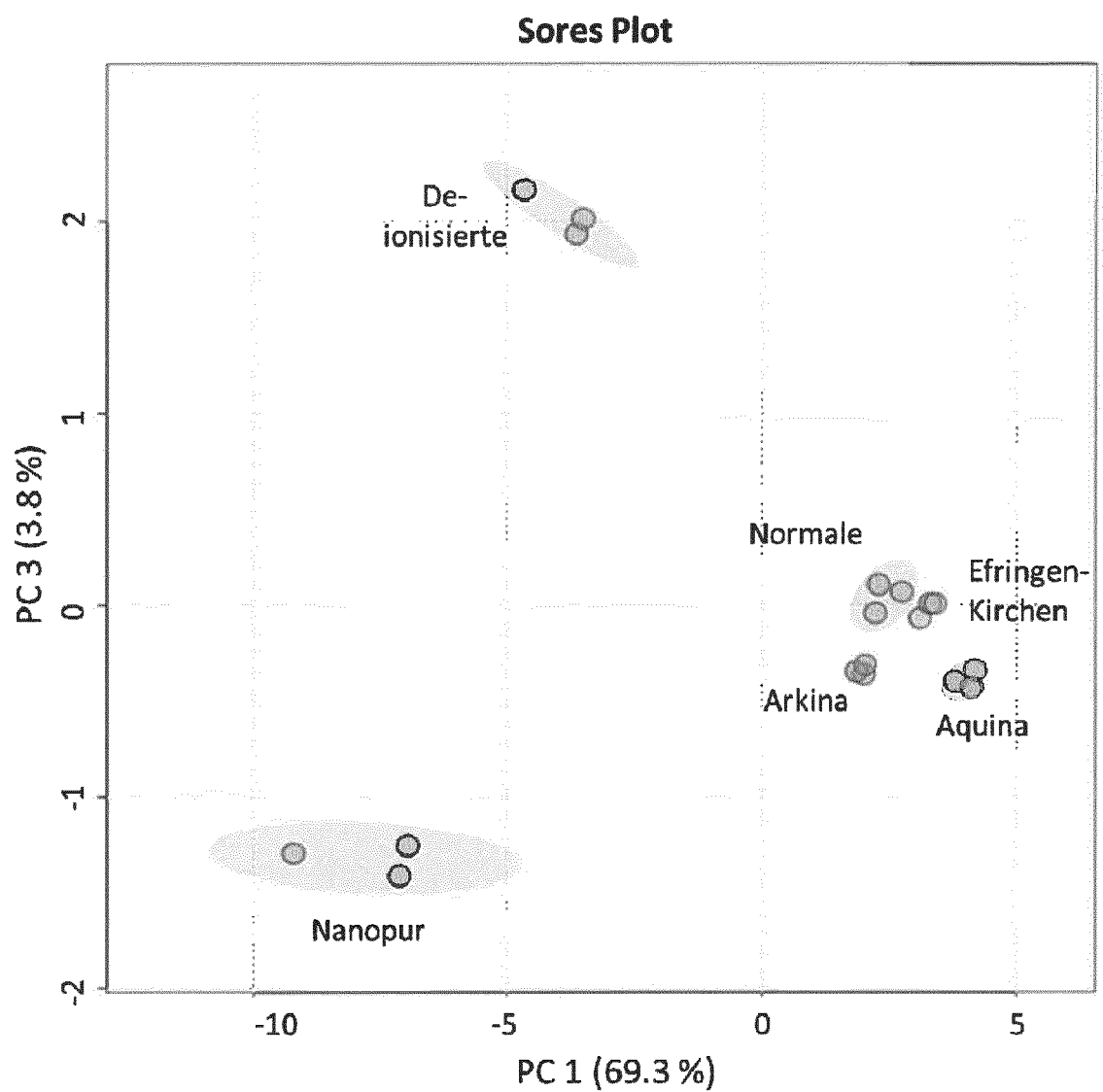
Figure 6:
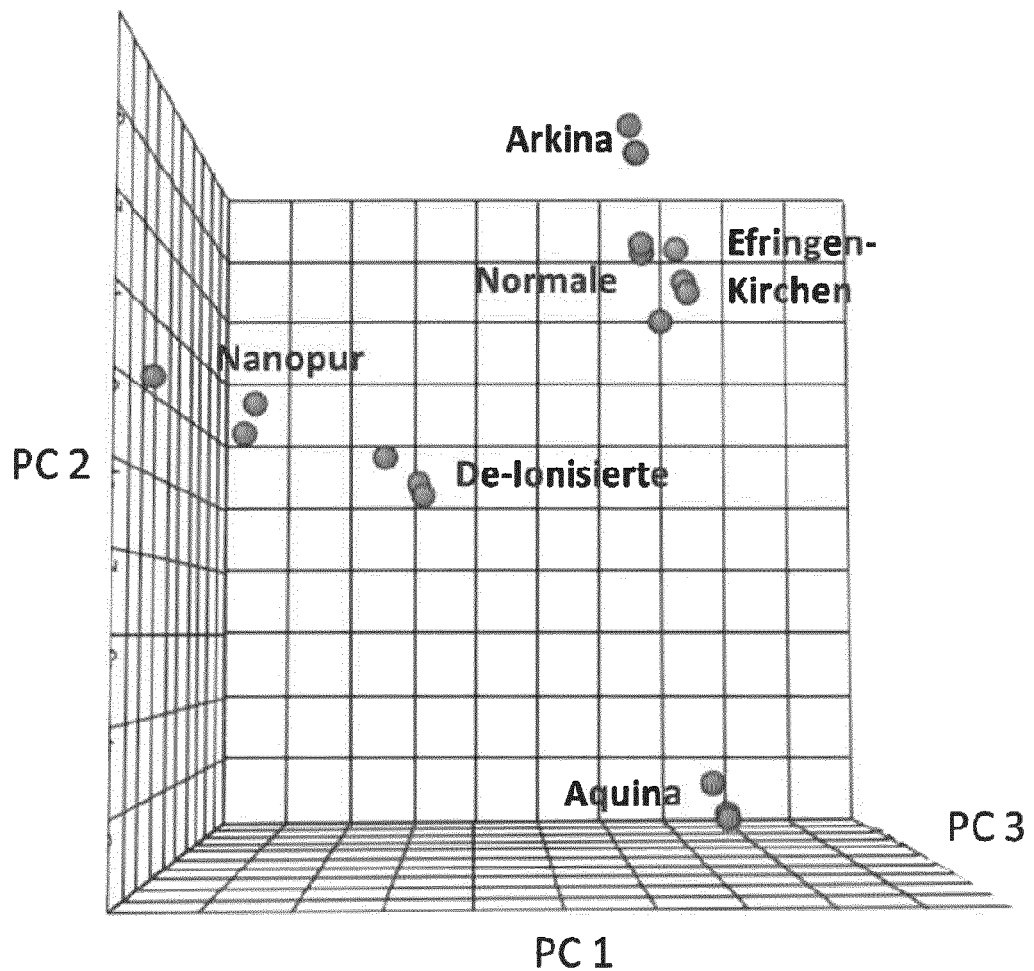

FIG. 4: Scores plot (PC1 versus PC2) of a Principal Component Analysis. The 95% confidence limits for samples from each source do not overlap representing a 100% separation of the sources FIG. 5: Scores plot (PC1 versus PC3) of a Principal Component Analysis. The 95% confidence limits for samples from each source do not overlap representing a 100% separation of the sources FIG. 6: Scores plot (PC1 versus PC3 versus PC2) of a Principal Component Analysis. All Clusters separate in the 3-dimensional projection.

Figure 7:
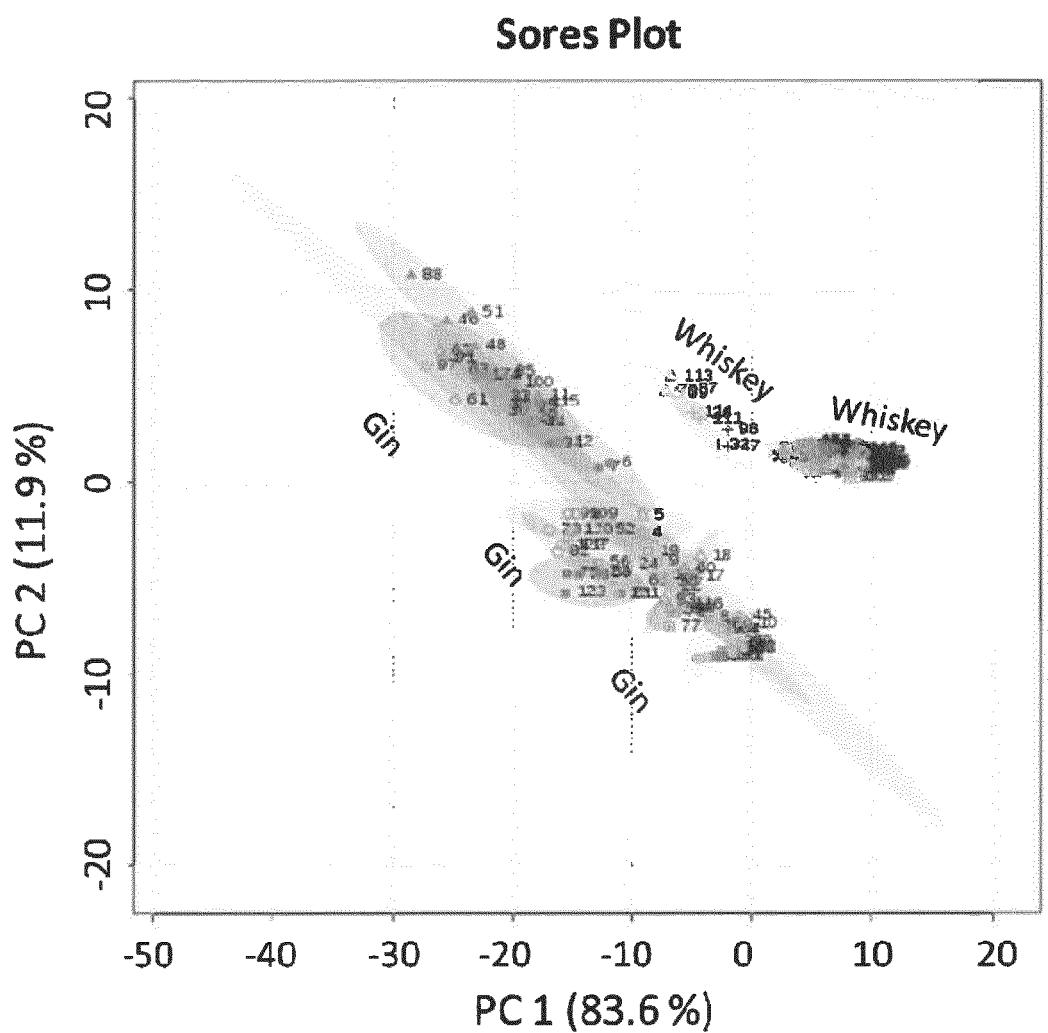

FIG. 7: Scores plot (PC1 versus PC2) of a Principal Component Analysis of a set of whiskey and gin samples. Gin samples (cluster bottom left) and whiskey samples (two clusters top right) separate clearly.

Figure 8:
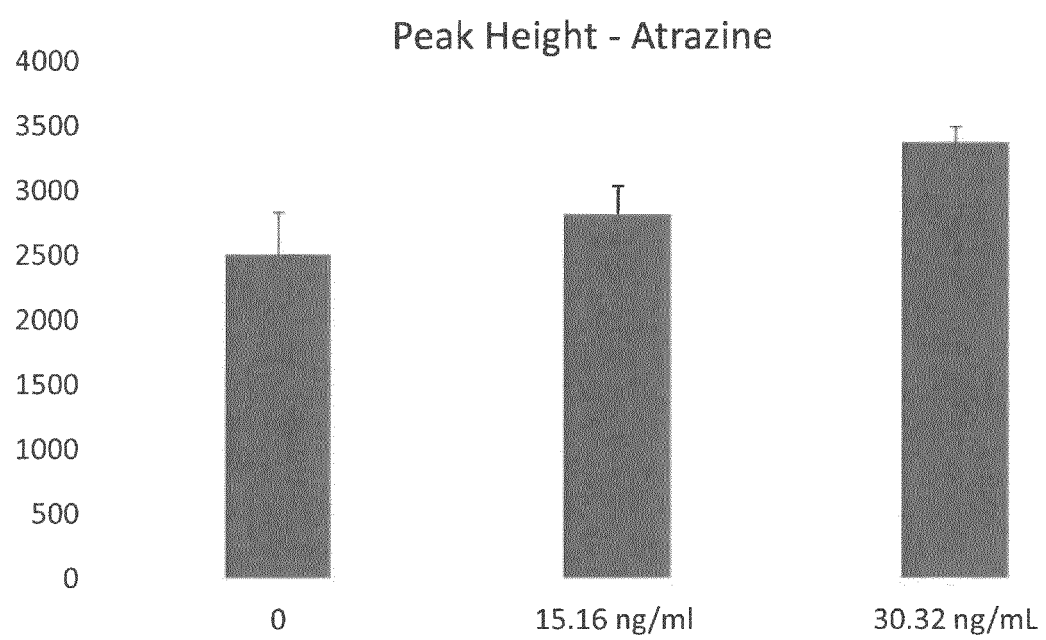

FIG. 8: Impact of adding Atrazine to wine samples—change of the signals of the Atrazin peak.

EXAMPLE 1

The following compounds were used in the exemplary method:
Sulfaguanidine—CAS number 57-67-0
Naproxen sodium—CAS number 26159-34-2
Sulfadimethoxine—CAS number 122-11-2
Ciprofloxacin—CAS number 85721-33-1
Tetracycline hydrochloride—CAS number 64-75-5
Verapamil hydrochloride—CAS number 152-11-4
Terfenadine—CAS number 50679-08-8
Leucine Enkephalin acetate salt hydrate—MDL number MFCD11045938
Reserpine—CAS number 50-55-5
Further Chemicals Used:
Water in-house system (Sartorius Arium Lab Water System, 18.2 MΩ)
Ethanol—CAS number 64-17-5 (Merck, LiChrosolv)
Acetonitrile—CAS number 75-05-8 (Fisher Chemicals, LC-MS Grade)
Formic acid—CAS number 64-18-6 (Fluka, MS Grade)
Liquid Handling System and MS:
Binary pump model G1312B (Agilent Technologies)
Autosampler model G1329A (Agilent Technologies)
Triple quadrupole mass spectrometer model 6460A (Agilent Technologies)
Electrospray source model G1958B (Agilent Technologies)
Sample Preparation A composition comprising the chemical compounds was prepared by adding 10 μg of each compound to 1 mL of Acetonitrile/Water 50/50 (v/v).

From a set of 3 different wines represented each by 5 bottles, a 1 mL sample was taken from each bottle with a Coravin™ Model Two Wine System and placed into a 1.5 mL Eppendorf PCR tube. The 15 tubes were centrifuged for 10 minutes at 12'500 g. A solution of water/ethanol 85/15 (v/v) was prepared and degassed with nitrogen for 5 minutes. The wine samples were placed into 15 different HPLC Vials and diluted with the water/ethanol solution 85/15 (v/v) by the addition of 16-volume of water/ethanol to one-volume of wine. After this step a volume of 10 μL of the composition comprising the chemical compound was added to the diluted wine and mixed 20 times with the push and pull function of the pipette. For example: 31 μL wine, 10 μL the composition comprising the compounds, 459 μL water/ethanol 85/15 (v/v) was mixed. The samples were placed randomized into an autosampler and subsequently measured by an LC-MS system.

Mass Spectrometry Method

The modular sample introduction system consisted of a degasser, a binary pump and an autosampler. For constant backpressure, a restriction capillary (0.12 mm ID, 2000 mm) was placed between the pump and the autosampler. The autosampler valve was connected with a 0.12 mm ID capillary directly to the electrospray source (ESI) without a column for compound separation. The mobile phase A consisted of water (channel A) and the mobile phase B of acetonitrile both containing 0.1% formic acid. An isocratic mixing was performed with 25% B with a constant flow rate of 600 µL/min. The measurement was done with one µL in flow injection analysis mode and the injection was done after 0.2 minutes. The stop time was set to 0.7 minutes. The ESI source was operated in positive mode with the following parameter settings: nebulizer pressure 45 psig, nozzle voltage 0 V, sheath gas flow 12 L/min, sheath gas temperature 375° C., drying gas flow 8 L/min, drying gas temperature 350° C., and capillary voltage at 3000 V. The mass spectrometer was run in a multi reaction monitoring mode at a dwell time of 40 millisecond per transition. The resolution of the first and second quadrupole was set to unit resolution 0.7 m/z F M (full width at half maximum). The cell accelerator voltage was fixed for all compounds to 4 V and the delta electro multiplier voltage was set to zero. The system was controlled under MassHunter Acquisition version 10 and the data analysis was done with MassHunter Quantitative Analysis version 10 and Microsoft Excel 2016.

Peak heights of the compounds were used for the subsequent multivariate data analysis. Peak heights of two subsequent measurements of the same sample were integrated and a data matrix was created with the peak heights as variables (columns) and integrated measurements as rows. Then variables were first auto-scaled (subtraction of the mean for each variable and subsequent division by the standard deviation of each variable). A Principal Component Analysis (PCA) was performed with the software Metaboanalyst 4.0. Scores were plotted for the first two exemplary compounds as shown in the FIGS. 1 and 2.

Parameters for Mass Spectrometry.

TABLE 1

| Compound | Fragmentor [V] | Precursor Ion [m/z] | Product Ion [m/z] | Collision Energy [V] |
|---|---|---|---|---|
| Reserpine | 195 | 609.3 | 195.1 | 41 |
| Leu-enkephalin | 128 | 556.3 | 120.1 | 58 |
| Terfenadine | 148 | 472.3 | 436.3 | 29 |
| Verapamil | 144 | 455.3 | 165.1 | 29 |
| Tetracycline | 97 | 445.1 | 410.1 | 17 |
| Ciprofloxacin | 135 | 332.1 | 314.2 | 21 |
| Sulfadimethoxine | 118 | 311.1 | 156.1 | 21 |
| Naproxen | 92 | 231.1 | 185.1 | 10 |
| Sulfaguanidine | 92 | 215.1 | 156.1 | 10 |

EXAMPLE 2

Identification of Water Samples

Water samples were analyzed from 6 different sources:
1. Aquina bottled mineral water.
2. Arkina bottled mineral water
3. Tap water from Muttenz (Switzerland) called ("Normale")
4. Tap water from Efringen Kirchen (Germany)
5. De-ionized water
6. Nanopur water (purified with a Nanopur lab water system)

3 samples of each source were analyzed by adding the following 29-compounds (integration of 3 injections per sample)

The following compounds were used in the exemplary method:

Leu-enkephalin acetate salt hydrate MDL N FCD11045938
Terfenadine—CAS number 50679-08-8
Verapamil hydrochloride—CAS number 152-11-4
Tetracycline hydrochloride—CAS number 64-75-5
Diltiazem hydrocloride—CAS number 33286-22-5
Linomycin hydrocloride—CAS number 859-18-7
Buspirone hydrocloride—CAS number 33386-08-2
Sarafloxacin hydrochloride hydrate—CAS number 91296-87-6
Haloperidol—CAS number 52-86-8
Trazodone hydrochloride—CAS number 25332-39-2
Ciprofloxacin—CAS number 85721-33-1
Quinine—CAS number 130-95-0
Ranitidin hydrochloride—CAS number 66357-59-3
Triclocarban—CAS number 101-20-2
Sulfadimethoxine—CAS number 122-11-2
Trimethoprim—CAS number 738-70-5
Amitriptyline hydrochloride—CAS number 549-18-8
Atenolol—CAS number 29122-68-7
Propranolol hydrochloride—CAS number 318-98-9
Sulfathiazole—CAS number 72-14-0
Sulfamethoxazole—CAS number 723-46-6
Cimetidin—CAS number 51481-61-9
Salbutamol—CAS number 18559-94-9
Melatonin—CAS number 73-31-4
Naproxen sodium—CAS number 26159-34-2
Atrazine—CAS number 1912-24-9
Sulfaguanidine—CAS number 57-67-0
Metformin hydrochloride—CAS number 1115-70-4
Reserpine—CAS number 50-55-5

Further Chemicals Used:
Water in-house system (Sartorius Arium Lab Water System, 18.2 MΩ)
Ethanol—CAS number 64-17-5 (Merck, LiChrosolv)
Acetonitrile—CAS number 75-05-8 (Fisher Chemicals, LC-MS Grade)
Formic acid—CAS number 64-18-6 (Fluka, MS Grade)

Liquid Handling System and MS:
Binary pump model G1312B (Agilent Technologies)
Autosampler model G1329A (Agilent Technologies)
Triple quadrupole mass spectrometer model 6460A (Agilent Technologies
Electrospray source model G1958B (Agilent Technologies)

Sample Preparation 6 different water samples were collected. From each sample three aliquots of 800 µL were mixed with 200 µL compound mixture (diluted mix of 29 compounds, with adjusted concentration in water/ethanol solution 85/15 (v/v). The samples were measured in a fully randomized order by an LC-MS system.

Liquid Handling, Mass Spectrometry and Data Analysis Methods

The modular sample introduction system consisted of a degasser, a binary pump and an autosampler. For constant backpressure, a restriction capillary (0.12 mm ID, 2000 mm) was placed between the pump and the autosampler. The autosampler valve was connected with a 0.12 mm ID capillary directly to the electrospray source (ESI) without a column for compound separation. The mobile phase A consisted of water (channel A) and the mobile phase B of acetonitrile both containing 0.1% formic acid. An isocratic mixing was performed with 25% B with a constant flow rate of 600 μL/min. The measurement was done with one μL in flow injection analysis mode and the injection was done after 0.2 minutes. The stop time was set to 0.7 minutes. The ESI source was operated in positive mode with the following parameter settings: nebulizer pressure 45 psig, nozzle voltage 0 V, gas flow 12 L/min, gas temperature 350° C., capillary voltage at 3000 V. The mass spectrometer was run in a multi reaction monitoring mode at a dwell time of 20 millisecond per transition. The resolution of the first and second quadrupole was set to unit resolution 0.7 m/z FWHM (full width at half maximum). The cell accelerator voltage was fixed for all compounds to 4 V and the delta electro multiplier voltage was set to zero. The system was controlled under MassHunter Acquisition version 10 and the data analysis was done with MassHunter Quantitative Analysis version 10 and Microsoft Excel 2016.

Peak heights of the compounds were used for the subsequent multivariate data analysis. Peak heights of two subsequent measurements of the same sample were integrated and a data matrix was created with the peak heights as variables (columns) and integrated measurements as rows. Then variables were first auto-scaled (subtraction of the mean for each variable and subsequent division by the standard deviation of each variable).

Subsequent multivariate data analysis (Hierarchical Cluster Analysis HCA, Principal Component Analysis PCA and Linear Discriminant Analysis) was performed with the heights of the measured peaks of all 29 compounds.

Qualitative Analyses (HCA and PCA, see FIGS. 3 to 5) showed a separation of all 6 samples of water. Further, it was found that similar sources (both tap water sources on the one hand and Nanopur/De-ionized water on the other hand) were more similar compared to other sources of water. In particular, the analyzed tap water samples (from Muttenz or Effringen-Kirchen) were similar. One sample of Muttenz of the triplicates clustered in the Effringen-Krichen cluster, which can be attributed to the similarity of tap water at both locations and to the fact that the cluster analysis is a non-supervised similarity search not optimized for discriminating different classes. Nonetheless, a distinction and thus identification of all water samples was observed since the supervised pattern Recognition Analysis with LDA of the samples showed a 100% classification of the 10-fold cross validated prediction of samples.

In summary, all sources of water were successfully discriminated using the herein described method.

TABLE 2

Parameters for mass spectrometry.

| Compound Name | Precursor Ion | MS1 Res | Product Ion | MS2 Res | Dwell | Fragmentor | Collision Energy | Cell Accelerator Voltage | Polarity |
|---|---|---|---|---|---|---|---|---|---|
| Leu-enkephalin | 556.3 | Unit | 120.1 | Unit | 20 | 128 | 58 | 4 | Positive |
| Terfenadine | 472.3 | Unit | 436.3 | Unit | 20 | 148 | 29 | 4 | Positive |
| Verapamil | 455.3 | Unit | 165.1 | Unit | 20 | 144 | 29 | 4 | Positive |
| Tetracycline | 445.1 | Unit | 410.1 | Unit | 20 | 97 | 17 | 4 | Positive |
| Diltiazem | 415 | Unit | 178 | Unit | 20 | 90 | 25 | 4 | Positive |
| Linomycin | 407.2 | Unit | 126.1 | Unit | 20 | 138 | 34 | 4 | Positive |
| Buspirone | 386.2 | Unit | 122.1 | Unit | 20 | 159 | 33 | 4 | Positive |
| Sarafloxacin | 385.8 | Unit | 342 | Unit | 20 | 130 | 16 | 4 | Positive |
| Haloperidol | 376.1 | Unit | 165 | Unit | 20 | 113 | 25 | 4 | Positive |
| Trazodone | 372.1 | Unit | 176.1 | Unit | 20 | 138 | 25 | 4 | Positive |
| Ciprofloxacin | 332.1 | Unit | 314.2 | Unit | 20 | 135 | 21 | 4 | Positive |
| Quinine | 325.2 | Unit | 160.1 | Unit | 20 | 113 | 31 | 4 | Positive |
| Ranitidin | 315.1 | Unit | 175.9 | Unit | 20 | 75 | 16 | 4 | Positive |
| Triclocarban | 315 | Unit | 162 | Unit | 20 | 130 | 13 | 4 | Positive |
| Sulfadimethoxine | 311.1 | Unit | 156.1 | Unit | 20 | 118 | 21 | 4 | Positive |
| Trimethoprim | 291 | Unit | 275 | Unit | 20 | 95 | 21 | 4 | Positive |
| Amitriptyline | 278.2 | Unit | 91.1 | Unit | 20 | 107 | 34 | 4 | Positive |
| Atenolol | 267.1 | Unit | 56.1 | Unit | 20 | 107 | 33 | 4 | Positive |
| Propranolol | 260.1 | Unit | 56.1 | Unit | 20 | 92 | 33 | 4 | Positive |
| Sulfathiazol | 256 | Unit | 156 | Unit | 20 | 85 | 9 | 4 | Positive |
| Sulfamethoxazol | 254 | Unit | 155.7 | Unit | 20 | 65 | 18 | 4 | Positive |
| Cimetidin | 253 | Unit | 158.9 | Unit | 20 | 110 | 10 | 4 | Positive |
| Salbutamol | 240.1 | Unit | 221.9 | Unit | 20 | 100 | 2 | 4 | Positive |
| Melatonin | 233 | Unit | 174 | Unit | 20 | 97 | 11 | 4 | Positive |
| Naproxen | 231.1 | Unit | 185.1 | Unit | 20 | 92 | 10 | 4 | Positive |
| Atrazin | 216.1 | Unit | 174 | Unit | 20 | 115 | 16 | 4 | Positive |
| Sulfaguanidine | 215.1 | Unit | 156.1 | Unit | 20 | 92 | 10 | 4 | Positive |
| Metformin | 130.1 | Unit | 60.2 | Unit | 20 | 75 | 15 | 4 | Positive |
| Reserpine | 609.3 | Unit | 195.1 | Unit | 20 | 195 | 41 | 4 | Positive |

Results

TABLE 3

|  | Aquina | Arkina | De-Ionized | Efringen | Nanopur | Normale |
|---|---|---|---|---|---|---|
| Aquina | 3 | | | | | |
| Arkina | | 3 | | | | |
| De-Ionized | | | 3 | | | |
| Efringen | | | | 3 | | |
| Nanopur | | | | | 3 | |
| Normale | | | | | | 3 |

EXAMPLE 3

Identification of Gin and Whisky 31 different Whisky samples and 16 different Gin samples were investigated. From each sample 5 aliquots were taken. The samples were measured with 29 compounds and classified (10-fold cross-validation, using the 29 peak heights) with a Linear Discriminant Analysis.

97.0% of the aliquots were attributed to the correct Gin or Whisky samples. This demonstrates that the herein provided method also can identify/authenticate Gin and Whisky.

The following compounds were used in the exemplary method:
  Leu-enkephalin acetate salt hydrate MDL N MFCD11045938
  Terfenadine—CAS number 50679-08-8
  Verapamil hydrochloride—CAS number 152-11-4
  Tetracycline hydrochloride—GAS number 64-75-5
  Diltiazem hydrocloride—CAS number 33286-22-5
  Linomycin hydrocloride—CAS number 859-18-7
  Buspirone hydrocloride—CAS number 33386-08-2
  Sarafloxacin hydrochloride hydrate—CAS number 91296-87-6
  Haloperidol—CAS number 52-86-8
  Trazodone hydrochloride—CAS number 25332-39-2
  Ciprofloxacin—CAS number 85721-33-1
  Quinine—CAS number 130-95-0
  Ranitidin hydrochloride—CAS number 66357-59-3
  Triclocarban—CAS number 101-20-2
  Sulfadimethoxine—CAS number 122-11-2
  Trimethoprim—CAS number 738-70-5
  Amitriptyline hydrochloride—CAS number 549-18-8
  Atenolol—CAS number 29122-68-7
  Propranolol hydrochloride—CAS number 318-98-9
  Sulfathiazole—CAS number 72-14-0
  Sulfamethoxazole—CAS number 723-46-6
  Cimetidin—CAS number 51481-61-9
  Salbutamol—CAS number 18559-94-9
  Melatonin—CAS number 73-31-4
  Naproxen sodium—CAS number 26159-34-2
  Atrazine—CAS number 1912-24-9
  Sulfaguanidine—CAS number 57-67-0
  Metformin hydrochloride—CAS number 1115-70-4
  Reserpine—CAS number 50-55-5
Further Chemicals Used:
  Water in-house system (Sartorius Arium Lab Water System, 18.2 MΩ)
  Ethanol—CAS number 64-17-5 (Merck, LiChrosolv)
  Acetonitrile—CAS number 75-05-8 (Fisher Chemicals, LC-MS Grade)
  Formic acid—CAS number 64-18-6 (Fluka, MS Grade)
Liquid Handling System and MS:
  Binary pump model G1312B (Agilent Technologies)
  Autosampler model G1329A (Agilent Technologies)
  Triple quadrupole mass spectrometer model 6460A (Agilent Technologies)
  Electrospray source model G1958B (Agilent Technologies)

Sample Preparation

From each Whisky or Gin sample, an aliquot of 100 µL was taken and mixed with 400 µL compound mixture, directly in 1.5 ml HPLC vial. The compound mixture of 29 compounds, with adjusted concentration in water/ethanol solution 85/15 (v/v) for each compound (see table below) was used.

Liquid Handling, Mass Spectrometry and Data Analysis Methods

The modular sample introduction system consisted of a degasser, a binary pump and an autosampler. For constant backpressure, a restriction capillary (0.12 mm ID, 2000 mm) was placed between the pump and the autosampler. The autosampler valve was connected with a 0.12 mm ID capillary directly to the electrospray source (ESI) without a column for compound separation. The mobile phase A consisted of water (channel A) and the mobile phase B of acetonitrile both containing 0.1% formic acid. An isocratic mixing was performed with 25% B with a constant flow rate of 600 µL/min. The measurement was done with one µL in flow injection analysis mode and the injection was done after 0.2 minutes. The stop time was set to 0.7 minutes. The ESI source was operated in positive mode with the following parameter settings: nebulizer pressure 45 psig, nozzle voltage 0 V, sheath gas flow 12 L/min, sheath gas temperature 350° C., a capillary voltage at 3000 V. The mass spectrometer was run in a multi reaction monitoring mode at a dwell time of 20 millisecond per transition. The resolution of the first and second quadrupole was set to unit resolution 0.7 m/z FWHM (full width at half maximum). The cell accelerator voltage was fixed for all compounds to 4 V and the delta electro multiplier voltage was set to zero. The system was controlled under MassHunter Acquisition version 10 and the data analysis was done with MassHunter Quantitative Analysis version 10 and Microsoft Excel 2016 . . . .

Peak heights of the compounds were used for the subsequent multivariate data analysis. Peak heights of two subsequent measurements of the same sample were integrated and a data matrix was created with the peak heights as variables (columns) and integrated measurements as rows. Then variables were first auto-scaled (subtraction of the mean for each variable and subsequent division by the standard deviation of each variable).

Subsequent multivariate data analysis (Hierarchical Cluster Analysis HCA, Principal Component Analysis PCA and Linear Discriminant Analysis) was performed with the heights of the measured peaks of all 29 compounds.

TABLE 4

Parameters for mass spectrometry.

| Compound Name | Precursor Ion | MS1 Res | Product Ion | MS2 Res | Dwell | Fragmentor | Collision Energy | Cell Accelerator Voltage | Polarity |
|---|---|---|---|---|---|---|---|---|---|
| Leu-enkephalin | 556.3 | Unit | 120.1 | Unit | 20 | 128 | 58 | 4 | Positive |
| Terfenadine | 472.3 | Unit | 436.3 | Unit | 20 | 148 | 29 | 4 | Positive |
| Verapamil | 455.3 | Unit | 165.1 | Unit | 20 | 144 | 29 | 4 | Positive |
| Tetracycline | 445.1 | Unit | 410.1 | Unit | 20 | 97 | 17 | 4 | Positive |
| Diltiazem | 415 | Unit | 178 | Unit | 20 | 90 | 25 | 4 | Positive |
| Linomycin | 407.2 | Unit | 126.1 | Unit | 20 | 138 | 34 | 4 | Positive |
| Buspirone | 386.2 | Unit | 122.1 | Unit | 20 | 159 | 33 | 4 | Positive |
| Sarafloxacin | 385.8 | Unit | 342 | Unit | 20 | 130 | 16 | 4 | Positive |
| Haloperidol | 376.1 | Unit | 165 | Unit | 20 | 113 | 25 | 4 | Positive |
| Trazodone | 372.1 | Unit | 176.1 | Unit | 20 | 138 | 25 | 4 | Positive |
| Ciprofloxacin | 332.1 | Unit | 314.2 | Unit | 20 | 135 | 21 | 4 | Positive |
| Quinine | 325.2 | Unit | 160.1 | Unit | 20 | 113 | 31 | 4 | Positive |
| Ranitidin | 315.1 | Unit | 175.9 | Unit | 20 | 75 | 16 | 4 | Positive |
| Triclocarban | 315 | Unit | 162 | Unit | 20 | 130 | 13 | 4 | Positive |
| Sulfadimethoxine | 311.1 | Unit | 156.1 | Unit | 20 | 118 | 21 | 4 | Positive |
| Trimethoprim | 291 | Unit | 275 | Unit | 20 | 95 | 21 | 4 | Positive |
| Amitriptyline | 278.2 | Unit | 91.1 | Unit | 20 | 107 | 34 | 4 | Positive |
| Atenolol | 267.1 | Unit | 56.1 | Unit | 20 | 107 | 33 | 4 | Positive |
| Propranolol | 260.1 | Unit | 56.1 | Unit | 20 | 92 | 33 | 4 | Positive |
| Sulfathiazol | 256 | Unit | 156 | Unit | 20 | 85 | 9 | 4 | Positive |
| Sulfamethoxazol | 254 | Unit | 155.7 | Unit | 20 | 65 | 18 | 4 | Positive |
| Cimetidin | 253 | Unit | 158.9 | Unit | 20 | 110 | 10 | 4 | Positive |
| Salbutamol | 240.1 | Unit | 221.9 | Unit | 20 | 100 | 2 | 4 | Positive |
| Melatonin | 233 | Unit | 174 | Unit | 20 | 97 | 11 | 4 | Positive |
| Naproxen | 231.1 | Unit | 185.1 | Unit | 20 | 92 | 10 | 4 | Positive |
| Atrazin | 216.1 | Unit | 174 | Unit | 20 | 115 | 16 | 4 | Positive |
| Sulfaguanidine | 215.1 | Unit | 156.1 | Unit | 20 | 92 | 10 | 4 | Positive |
| Metformin | 130.1 | Unit | 60.2 | Unit | 20 | 75 | 15 | 4 | Positive |
| Reserpine | 609.3 | Unit | 195.1 | Unit | 20 | 195 | 41 | 4 | Positive |

EXAMPLE 4

Analysis with One Compound Only

Analysis of Classes Gin Versus Whisky

The above-mentioned combined Whisky and gin data set was re-analyzed but this time the classes "Whisky" versus "Gin" had to be correctly assigned to each aliquot. LDA models were built and samples were classified in a 10-fold cross-validation procedure.

For models using the peak heights of all 29 compounds, 100% correct prediction of the classes "Gin" versus "Whisky" were achieved.

For LDA models using peak heights of only 1 compound, prediction performances of 68.5% to 100% were achieved (average 87.5%, standard deviation 7.1%). Two markers (Quinine and Sarafloxacin) allowed a 100% correct classification each on its own. This demonstrates that for predictions with few classes involved single compound approaches can be used.

EXAMPLE 5

Identification of Robustness by Spiking Atrazine and Quinine

To investigate the impact of contaminations of samples with the identical chemicals, which are used in the method as compounds, on the compound signals, spiking experiments with Atrazine and Quinine were performed (Atrazine and Quinine were both compounds used in the experiments). Thus, Atrazine and Quinine were already comprised in the sample and additional Atrazine and Quinine were added to the sample in different concentrations, as a representative of the at least one compound, Atrazine study: 3 samples of wine prepared: One original wine sample, one sample spiked with 15.16 ng/mL Atrazine and one sample with 30.32 ng/mL Atrazine. Thus, Atrazine was added to two of the three wine samples in different concentrations as indicated.

Quinine study: 2 samples of wine were prepared: one original wine sample, one sample spiked with 0.25 mg/mL Quinine. Thus, Quinine was added to one of the wine sample.

Samples were measured in triplicates and peaks were analyzed. In the Atrazine study, spiking 15.16 ng/mL of Atrazine resulted in a non-significant increase of the Atrazine peak heights while spiking 30.32 ng/mL Atrazin resulted in a significant increase of the Atrazine peak height (see FIG. 8). Peak heights of all other compounds were not impacted.

In the Quinine study, the addition of 0.25 mg/ml caused a significant increase of the Quinine peak height while other peaks were not affected.

Thus, spiking of substances representing specific compounds of the herein proposed analysis system will cause increases of these compounds. Therefore, the sample can also be identified if the at least one compound is already comprised in the sample and the same compound is added to sample such that the level of said compound is increased. Further, the potential influence of atrazine or quinine contamination in wine or other samples would not influence the overall identification. It might influence the signal of this marker, which would contribute to the identification of such contaminated sample batches and thus can further improve the identification/authentication of a sample.

The invention claimed is:
1. A method for identifying and/or authenticating a sample, wherein the method comprises the steps of:

(i) adding at least one compound to the sample, wherein the at least one compound has a variable ionization;
(ii) obtaining a mass spectrum of the at least one compound and determining a level of the at least one compound after addition to the sample;
(iii) comparing the level of the at least one compound determined in (ii) to a reference level, wherein the reference level is a level of the same compound determined after addition to a reference sample; and
(iv) identifying the sample based on the comparison in step (iii) and the effect of the sample on the level of the at least one compound.

2. The method of claim 1, wherein the level is (a) mass spectrometry signal level(s), in particular wherein the level is the abundance determined in the mass spectrum.

3. The method according to claim 1, wherein the sample has an ion suppression, or has an ion enhancement effect on the at least one compound or wherein the sample does not substantially alter the ionization of the at least one compound.

4. The method according to claim 1, wherein the ion suppression efficiency or the ion enhancement efficiency of the sample on the at least one compound is determined, and said ion suppression efficiency or said ion enhancement efficiency is compared to the ion suppression efficiency or to the ion enhancement efficiency of the reference sample on the same at least one compound, and based thereon the sample is identified.

5. The method according to claim 1,
wherein a similar or an identical level of the at least one compound compared to the reference level indicates that the sample corresponds to the reference sample; or
wherein a difference in the level of the at least one compound as compared to the reference level indicates that the sample does not correspond to the reference sample.

6. The method according to claim 1, wherein in step (iv) the sample is identified based on the particular pattern of ion suppression or ion enhancement of the at least one compound.

7. The method according to claim 1, wherein a sample is used in step (i) without experiencing a separation step, suitably such that the level(s) in step (ii) are determined without a chromatographic separation, and preferably wherein the mass spectrum is obtained by a mass spectrometer coupled to an ion source, in particular an electrospray ionization.

8. The method according to claim 1,
wherein in step (i) different concentrations of the at least one compound are added to the sample, and wherein in step (ii) the levels of the different concentrations of the at least one compound after addition to the sample are determined; or
wherein in step (i) the at least one compound is added to different concentrations of the sample and wherein in step (ii) the levels of the at least one compound after addition to the samples are determined.

9. The method according to claim 1,
wherein the method comprises to generate a dose response curve, in particular wherein the dose response curve is based on the levels of different concentrations of the at least one compound; or
wherein the dose response curve is based on the levels of the at least one compound after addition to said different concentrations of said sample.

10. The method according to claim 1, wherein in step (i) 1 to 100 compounds are added.

11. The method according to claim 1, wherein the compounds are susceptible to an ion suppression and/or ion enhancement effect of particular substances comprised in the sample.

12. The method according to claim 1, wherein the compounds are distinguishable in the mass spectrum.

13. The method according to claim 1, wherein the compounds have a high or low molecular weight, a different partition coefficient (log P), and/or a different pka.

14. The method according to claim 1, wherein in step (ii) the level of each of the at least one compound is determined, and wherein in step (iii) the level of each of the at least one compound is compared to each reference level.

15. The method according to claim 1, wherein the at least one compound is not comprised in the sample.

16. The method according to claim 1, wherein the at least one compound is selected from the group consisting of sulfaguanidine, naproxen sodium, sulfadimethoxine, ciprofloxacin, tetracycline hydrochloride, verapamil hydrochloride, terfenadine, leucine enkephalin acetate salt hydrate and reserpine.

17. The method according to claim 1, wherein the at least one compound has a concentration in the sample of at least 5 times the limit of quantification after addition to the sample.

18. The method according to claim 1, wherein the at least one compound has a concentration in the sample after addition to the sample to suppress and/or enhance the level of the least one compound to about 20% to about 80% in comparison to the level of the same compound determined in the absence of the sample.

19. The method according to claim 1, wherein further levels of a standard are determined, in particular for calibrating the method of any of the preceding claims.

20. The method according to claim 1, wherein the sample is a pooled sample suitable for the use in quality control.

21. The method according to claim 1, wherein the sample is selected from the group consisting of wine, spirituous beverage, foodstuff, processed foodstuff, tea, coffee, herb extract, natural product, natural products extracts, beer, fruit juice (for example orange and apple), a pharmaceutical composition, a formulation of a pharmaceutical, a body fluid, tissue extract, blood, blood plasma, blood serum, and urine.

22. The method according to claim 1, wherein the reference sample allows the identification and/or authentication of the sample.

23. The method according to claim 1, wherein the sample and the reference sample are from the same sort.

24. The method according to claim 1, wherein the reference sample is an authentic sample or a sample with a known composition.

25. The method according to claim 1, wherein the reference sample is a wine sample of particular vintage, of a particular grape variety, or from a particular region, or from a particular producer.

26. The method according to claim 1, wherein the identification of the sample is the identification of a dilution of the sample,
in particular wherein the dilution of the sample is identified based on the comparison of the dose response curve of the sample to the dose response curve of the reference sample,
in particular wherein the dose response curves are based on the levels of the different concentrations of the at least one compound or the level of a constant concentration of the at least one compound.

27. The method according to claim 1, wherein the method comprises a calibration step, wherein the sample comprises known compounds with known variable ionization and/or known ionization effects, such as a known ion suppression effect on the at least one compound, a known ion enhancement effect on the at least one compound or known to not substantially alter the level of the at least one compound, and wherein the sample is used to calibrate the method and/or the instruments employed in any one of the preceding claims.

* * * * *